(12) United States Patent
Motadel

(10) Patent No.: US 9,649,636 B2
(45) Date of Patent: May 16, 2017

(54) PIPETTE TIP HANDLING DEVICES AND METHODS

(71) Applicant: BIOTIX, INC., San Diego, CA (US)

(72) Inventor: Arta Motadel, San Diego, CA (US)

(73) Assignee: BIOTIX, INC., San Diego, CA (US)

( * ) Notice: Subject to any disclaimer, the term of this patent is extended or adjusted under 35 U.S.C. 154(b) by 0 days.

(21) Appl. No.: 15/331,495

(22) Filed: Oct. 21, 2016

(65) Prior Publication Data
US 2017/0080433 A1  Mar. 23, 2017

Related U.S. Application Data

(63) Continuation of application No. 14/981,596, filed on Dec. 28, 2015, now Pat. No. 9,505,006, which is a continuation of application No. 13/773,527, filed on Feb. 21, 2013, now Pat. No. 9,238,227, which is a continuation of application No. 12/422,250, filed on Apr. 11, 2009, now Pat. No. 8,460,622.

(60) Provisional application No. 61/044,243, filed on Apr. 11, 2008.

(51) Int. Cl.
*B01L 9/00* (2006.01)
*B01L 3/02* (2006.01)
*B65D 85/62* (2006.01)
*G01N 35/04* (2006.01)
*G01N 35/10* (2006.01)

(52) U.S. Cl.
CPC ............. *B01L 9/543* (2013.01); *B01L 3/0275* (2013.01)

(58) Field of Classification Search
CPC .. B01L 9/543; B01L 3/0275; B01L 2200/025; B01L 2200/14; B01L 2300/0809; B65D 85/62; G01N 2035/0427; G01N 2035/103
See application file for complete search history.

(56) References Cited

U.S. PATENT DOCUMENTS

| | | | | |
|---|---|---|---|---|
| 5,779,984 A | * | 7/1998 | Kelly | B65D 25/108 206/486 |
| 7,169,361 B2 | * | 1/2007 | Arnold, Jr. | B01L 9/543 206/562 |
| 8,460,622 B2 | * | 6/2013 | Motadel | B01L 9/543 211/126.1 |
| 8,590,736 B2 | * | 11/2013 | Motadel | B01L 9/543 221/104 |
| 9,238,227 B2 | * | 1/2016 | Motadel | B01L 9/543 |

* cited by examiner

*Primary Examiner* — Brian R Gordon
(74) *Attorney, Agent, or Firm* — Grant IP, Inc.

(57) ABSTRACT

Discussed herein are methods and devices for storing, handling, loading or dispensing of pipette tips. Some embodiments allow repetitive loading of an array of multiple pipette tips that are stored in a nested configuration.

24 Claims, 10 Drawing Sheets

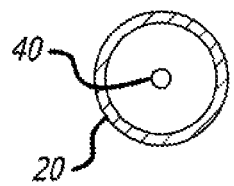
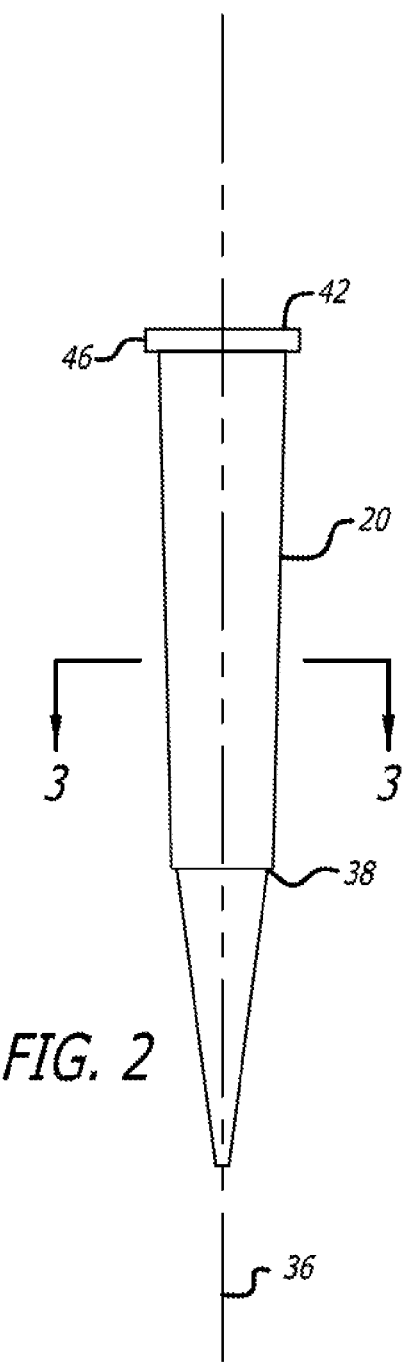
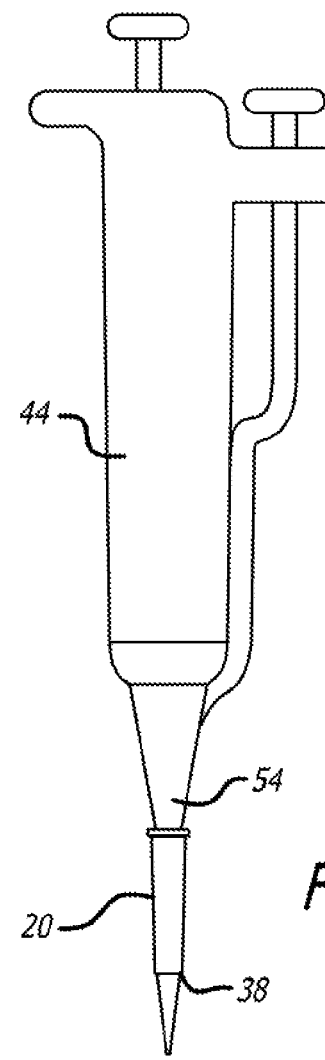

PIPETTE TIP HANDLING DEVICES AND METHODS

CROSS REFERENCE TO RELATED APPLICATIONS

This patent application is a continuation of U.S. patent application Ser. No. 14/981,596 filed on Dec. 28, 2015, now U.S. Pat. No. 9,505,006, entitled PIPETTE TIP HANDLING DEVICES AND METHODS, naming Arta Motadel as an inventor, which is a continuation of U.S. patent application Ser. No. 13/773,527 filed on Feb. 21, 2013, now U.S. Pat. No. 9,238,227, entitled PIPETTE TIP HANDLING DEVICES AND METHODS, naming Arta Motadel as an inventor, which is a continuation of U.S. patent application Ser. No. 12/422,250 filed on Apr. 11, 2009, now U.S. Pat. No. 8,460,622, entitled PIPETTE TIP HANDLING DEVICES AND METHODS, naming Arta Motadel as an inventor, which claims the benefit of U.S. Provisional Patent Application No. 61/044,243, filed on Apr. 11, 2008, entitled PIPETTE TIP HANDLING DEVICES AND METHODS, naming Arta Motadel as an inventor. The entire content of the foregoing patent applications is hereby incorporated by reference, including all text, tables and drawings.

RELATED PATENT APPLICATION

This patent application is a continuation of U.S. patent application Ser. No. 14/981,596 filed on Dec. 28, 2015, entitled PIPETTE TIP HANDLING DEVICES AND METHODS, naming Arta Motadel as an inventor, which is a continuation of U.S. patent application Ser. No. 13/773,527 filed on Feb. 21, 2013, now U.S. Pat. No. 9,238,227, entitled PIPETTE TIP HANDLING DEVICES AND METHODS, naming Arta Motadel as an inventor, which is a continuation of U.S. patent application Ser. No. 12/422,250 filed on Apr. 11, 2009, now U.S. Pat. No. 8,460,622, entitled PIPETTE TIP HANDLING DEVICES AND METHODS, naming Arta Motadel as an inventor, which claims the benefit of U.S. Provisional Patent Application No. 61/044,243, filed on Apr. 11, 2008, entitled PIPETTE TIP HANDLING DEVICES AND METHODS, naming Arta Motadel as an inventor. The entire content of the foregoing patent applications is hereby incorporated by reference, including all text, tables and drawings.

FIELD OF THE INVENTION

Described herein are method and device embodiments for storing, loading or handling of pipette tips. Some embodiments allow for convenient loading of multiple batches of pipette tips into loading blocks or plates with a minimal amount of waste.

BACKGROUND

Pipette tips are used in large quantities for a wide variety of applications related to liquid material handling, such as measuring, dispensing and aspirating of the liquids. Pipette tips are often used in conjunction with hand held pipettors, such as mechanical or electrical pipettors, that have distal nozzles that are configured to be releasably engaged with a proximal port or opening of a pipette tip in a sealed relationship. The pipettor may then be used to apply a vacuum or otherwise decrease the pressure in the interior volume of the pipette tip in order to aspirate liquid into the pipette tip for transfer to another location. For some applications a single pipettor may be used, however, for some applications, particularly automated or robotic applications, pipettors or manifolds having multiple distal nozzles may be used to engage multiple pipettor tips disposed in a loading plate or block simultaneously.

For such configurations, after the pipette tips are seated onto the nozzles and removed from the loading block, a new set of pipette tips must be provided for the next cycle of liquid handling. Typically, a new set of pipette tips are taken from a package in a storage plate and loading block in a regularly spaced array and positioned for seating with the distal nozzles of the manifold. Because of the difficulty of manually handling large numbers of pipette tips due to the time consuming nature of such handling as well as the risk of contamination, pipette tips are generally pre-packaged in regularly spaced arrays spaced in pre-determined spacing to match the spacing of the array of distal nozzles. The pipette tips may be transferred from the packaging in a loading plate that is part of the packaging but may also include an entire loading plate and loading block in order to maintain the array configuration during handling and transfer to a location for seating to the manifold or pipettor.

For such multiple pipette tip arrays, because each pipette tip may require a significant amount of axial force between the respective nozzle and proximal opening of the pipette tip in order to be properly seated, the cumulative force required to seat an array of pipette tips may be quite high. For example, a 96 tip manifold may exert about 75 pounds to about 250 pounds of force on a loading block having a 96 tip array. Because of the amount of force generated, the loading block that supports the loading plate must be structurally strong and able to withstand the cumulative axial force without significant deformation. To be this strong, the block requires a significant amount of mass of material which is typically a polymer. Once the distal nozzles of the manifold have engaged and seated the pipette tips and withdrawn them from the loading plate and block, the loading block and plate are disposed of and replaced with a new loading block and plate that is full of new pipette tips. As a result, a user performing a high volume of such liquid handling cycles will be disposing of a large volume of loading blocks and plates which generates a large volume of polymer waste which may be environmentally unsound in many instances.

For embodiments of pipette tip arrays that transfer in a loading plate without the loading block, the loading tray is lifted or moved from the packaging, as necessary, and positioned over a loading block. After each seating of an array of pipette tips, the loading plate must be removed or the z-axis position of the top of the plate will change with the addition of each new loading plate from a new package of pipette tips.

SUMMARY

Some embodiments of a pipette tip dispensing device, include a displacement actuator having an actuator housing with a top portion, four sides, and an inner surface. The actuator housing also has a plurality of regularly spaced detent members disposed on at least one side of the housing and a plurality of proximal alignment members disposed in a regularly spaced array on a top portion of the actuator with each proximal alignment member configured to releasably engage and restrict lateral displacement of a proximal end of a pipette tip engaged therewith. An alignment housing of the device includes an outside surface in contact with the inside surface of the displacement actuator housing in a sliding arrangement. A plurality of regularly spaced detent members are configured to releasably engage the detent members of the actuator housing. In addition, the detent members of the alignment housing have a regular spacing that is substantially the same as the regular spacing of the detent members of the actuator housing. A proximal opening of the alignment housing has an inside surface configured to engage outer lateral sides of a loading block. A distal barrier element is disposed at a top portion of the alignment housing and includes a plurality of restrictive apertures which are substantially aligned with corresponding proximal alignment members.

Some embodiments of a pipette tip dispensing device include a displacement actuator having an actuator housing that includes an inside surface, a clear thin rigid material formed into a substantially rectangular configuration with an open bottom portion, substantially planar sides and a plurality of regularly spaced detent members disposed on at least one sides thereof. A proximal actuator plate (also referred to herein as an "activator plate") of the actuator includes a plurality of proximal alignment members disposed substantially in a plane in a regularly spaced array and each proximal alignment member configured to releasably engage and restrict lateral displacement of a proximal end of a pipette tip engaged therewith. An alignment housing assembly of the device includes a substantially rectangular structure having an outside surface configured to engage the inside surface of the actuator housing, four sides formed from a clear thin substantially rigid material with a plurality of regularly spaced detent members configured to releasably engage the detent members of the actuator housing and having a regular spacing that is substantially the same as the regular spacing of the detent members of the actuator housing. A proximal opening of the alignment housing is configured to engage an outside perimeter of a loading block. An outer surface of the alignment housing is configured to slidingly engage an inner surface of the actuator housing so as to allow relative movement therebetween. A substantially planar distal barrier element is disposed at a top portion of the alignment housing and has a plurality of restrictive apertures which are substantially aligned with respective proximal alignment members and which are configured to engage an outside surface of a pipette tip, restrict lateral displacement of a pipette tip and resist axial displacement of the pipette tip until an axial force threshold imparted to the pipette tip is reached. Once a threshold axial force is imparted to a pipette tip engaged by restrictive aperture, the pipette tip will pass through the restrictive aperture so as to be dispensed.

Some embodiments of a method of simultaneously dispensing an array of multiple pipette tips into a loading block, include providing a dispensing device that includes an array of regularly spaced pipette tips and engaging the dispensing device with a loading block such that distal ends of pipette tips which are engaged with restrictive apertures of a barrier member of the dispensing device are disposed within receptacles of the loading block. Thereafter, an actuator of the dispensing device is actuated so as to apply an axial force on the array of pipette tips engaged with the restrictive apertures of the dispensing device until a threshold axial force is applied and the array of pipette tips engaged with the restrictive apertures is dispensed into respective receptacles in the loading block.

In some embodiments, provided herein is a pipette tip dispensing device, comprising a displacement actuator which includes an actuator housing having a top portion, four sides, and an inner surface, a plurality of regularly spaced detent members disposed on at least one side of the housing, and a plurality of proximal alignment members disposed in a regularly spaced array on a top portion of the actuator with each proximal alignment member configured to releasably engage and restrict lateral displacement of a proximal end of a pipette tip engaged therewith. The device also comprises an alignment housing including an outside surface in contact with the inside surface of the displacement actuator housing in a sliding arrangement, a plurality of regularly spaced detent members configured to releasably engage the detent members of the actuator housing and having a regular spacing that is substantially the same as the regular spacing of the detent members of the actuator housing, and a proximal opening having an inside surface configured to engage outer lateral sides of a loading block 26. The device also comprises a distal barrier element disposed at a top portion of the alignment housing having a plurality of restrictive apertures which are substantially aligned with corresponding proximal alignment members.

In certain embodiments, the pipette tip dispensing device further comprises a plurality of pipette tips disposed in a nested, regularly spaced array between the respective proximal alignment members and restrictive apertures with a longitudinal axis of each nested set of pipette tips being substantially aligned and coaxial with the respective proximal alignment members and restrictive apertures. The regular spacing of the restrictive apertures and proximal alignment members can be about 9 mm. The proximal alignment members comprise cone shaped abutments extending from a distal surface of the proximal actuator plate.

In some embodiments, a pipette tip dispensing device has actuator housing and alignment housing comprised of a polymer material. The polymer material of the actuator housing and alignment housing comprises molded polypropylene in some embodiments. The polymer material of the actuator housing and alignment housing comprises a thickness of about 0.005 inches to about 0.05 inches in certain embodiments.

Provided also is a pipette tip dispensing device having an actuator housing comprised of a telescoping arrangement which has multiple housing elements. The restrictive apertures of the barrier element comprise holes sized to mechanically engage a major outer transverse dimension of a proximal portion of a pipette tip and prevent axial displacement of the proximal portion through the aperture until a threshold axial force is applied to the engaged pipette tip at which time the proximal portion is deflected and compressed to allow passage through the restrictive aperture.

In some embodiments, provided is a pipette tip dispensing device, comprising a displacement actuator comprising an actuator housing that includes an inside surface, a clear thin rigid material formed into a substantially rectangular configuration with an open bottom portion, substantially planar sides and a plurality of regularly spaced detent members disposed on at least one sides thereof, and a proximal actuator plate having a plurality of proximal alignment members disposed substantially in a plane in a regularly spaced array and each proximal alignment member configured to releasably engage and restrict lateral displacement of a proximal end of a pipette tip engaged therewith; an alignment housing assembly including a substantially rectangular structure having an outside surface configured to engage the inside surface of the actuator housing, four sides formed from a clear thin substantially rigid material with a plurality of regularly spaced detent members configured to releasably engage the detent members of the actuator housing and having a regular spacing that is substantially the same as the regular spacing of the detent members of the actuator housing, and a proximal opening configured to engage an outside perimeter of a loading block, an outer surface configured to slidingly engage an inner surface of the actuator housing so as to allow relative movement there between; and a substantially planar distal barrier element disposed at a top portion of the alignment housing having a plurality of restrictive apertures which are substantially aligned with respective proximal alignment members and which are configured to engage an outside surface of a pipette tip, restrict lateral displacement of a pipette tip and resist axial displacement of the pipette tip until an axial force threshold imparted to the pipette tip is reached.

In certain embodiments, the pipette tip dispensing device further comprises a plurality of pipette tips disposed in a nested, regularly spaced array between the respective proximal alignment members and restrictive apertures with a longitudinal axis of each nested set of pipette tips being substantially aligned and coaxial with the respective proximal alignment members and restrictive apertures. In this embodiment, the pipette tip dispensing device can have restrictive apertures and proximal alignment members having regular spacing about 9 mm. The pipette tip dispensing device also can have proximal alignment members comprising cone shaped abutments extending from a distal surface of the proximal actuator plate. The pipette tip dispensing device can have an actuator housing and alignment housing comprising a polymer material. The polymer material of the actuator housing and alignment housing can comprise molded polypropylene. The polymer material of the actuator housing and alignment housing can comprise a thickness of about 0.005 inches to about 0.05 inches. The actuator housing can also comprise a telescoping arrangement having multiple housing elements. The restrictive apertures of the barrier element can also comprise holes sized to mechanically engage a major outer transverse dimension of a proximal portion of a pipette tip and prevent axial displacement of the proximal portion through the aperture until a threshold axial force is applied to the engaged pipette tip at which time the proximal portion is deflected and compressed to allow passage through the restrictive aperture.

Also provided is a method of simultaneously dispensing an array of multiple pipette tips into a loading block, which comprises providing a dispensing device that includes an array of regularly spaced pipette tips; engaging the dispensing device with a loading block such that distal ends of pipette tips which are engaged with restrictive apertures of a barrier member of the dispensing device are disposed within receptacles of the loading block; actuating an actuator of the dispensing device so as to apply an axial force on the array of pipette tips engaged with the restrictive apertures of the dispensing device to overcome a threshold axial force and eject the array of pipette tips engaged with the restrictive apertures into respective receptacles in the loading block.

In some embodiments, the dispensing device further comprises a plurality of pipette tips disposed in a nested, regularly spaced array between respective proximal alignment members and restrictive apertures with a longitudinal axis of each nested set of pipette tips being substantially aligned and coaxial with the respective proximal alignment members and restrictive apertures and further comprising multiple actuations of the actuator in order to eject a plurality of arrays of multiple pipette tips.

In certain embodiments, the actuator further comprises a plurality of regularly spaced proximal alignment members configured as cone shaped abutments extending from a distal surface of a proximal actuator plate, the barrier member comprises a barrier plate and where actuating the actuator comprises moving the proximal actuator plate towards the barrier plate with threshold axial force sufficient to force an array of pipette tips through the restrictive apertures of the barrier plate.

In some embodiments, the actuator housing and alignment housing comprise a clear polymer material and further comprising visualizing the ejection of the array of multiple pipette tips from the restrictive apertures of the barrier member during actuation. The actuator housing can comprise a telescoping arrangement having multiple housing elements and where actuation of the actuator comprises collapsing the multiple housing elements from an extended state to a collapsed nested state. The restrictive apertures of the barrier element can comprise holes sized to mechanically engage a major outer transverse dimension of a proximal portion of a pipette tip and prevent axial displacement of the proximal portion through the aperture until a threshold axial force is applied to the engaged pipette tip and further comprising actuating the actuator until the proximal portion of each pipette tip of the array of multiple pipette tips engaged with the restrictive apertures are deflected and compressed to allow passage through the restrictive apertures and barrier member.

Provided in some embodiments is a pipette tip dispensing device, comprise (a) a housing; (b) a distal barrier plate in effective connection with the housing; and (c) a plurality of nested pipette tip units where each unit is aligned with a channel in the distal barrier plate, and where the distal barrier plate comprises (i) a plurality of channels, where each channel has a diameter larger than the widest portion of a pipette tip; (ii) a top surface, and (iii) a bottom surface that comprises a plurality of tails around some or all of the channels, where: (1) the tails extend in a nearly perpendicular orientation from the bottom surface, and (2) the tails around each channel contact a pipette tip when a pipette tip is dispensed and passes by the tails, thereby imparting (e.g., applying) a frictional force on the pipette tip when it is dispensed. In some embodiments, the tails deflect outwards against the pipette tip before, and/or at the same time the pipette tip is being dispensed (e.g., the pipette tip is translating), and sometimes the tails contact the proximal portion of a pipette tip. In some embodiments, a subset of channels in the distal barrier plate are surrounded by tails that eject pipette tips of an array at one time, and another subset of channels in the plate are surrounded by tails that eject pipette tips of the same array at another time. A distal barrier plate may include 2, 3, 4, 5, 6, 7, 8, 9, 10, 11, 12, 13, 14, 15, 16, 17, 18, 19 or 20 of such subsets of channels.

In some embodiments pertaining to a dispensing device described in the preceding paragraph, the top surface and/or the bottom surface is substantial flat or planar. In certain embodiments, each channel in the dispensing device can comprise 2, 3, 4, 5, 6, 7, 8, 9, 10 or more tails. Each channel of the barrier plate can comprise tails of the same length. In some embodiments, each channel of the barrier plate can comprise tails of different lengths in some embodiments. Channels located in the center of the barrier plate can comprise the longest tails. In certain embodiments, channels located in the center of the barrier plate can comprise the shortest tails. Subsequent channels concentrically disposed about a central longitudinal axis can comprise sequentially shorter tails in length in a stepwise manner in some embodiments. In certain embodiments, subsequent channels concentrically disposed about a central longitudinal axis can comprise sequentially longer tails in length in a stepwise manner. Channels located in the center of the barrier plate along the X axis can comprise tails of the same length and channels along the Y axis comprise tails of varying length in some embodiments. Channels located in the center of the barrier plate along the Y axis can comprise tails of the same length and channels along the X axis comprise tails of varying length in certain embodiments. Channels located in the center of the barrier plate along the X and Y axes can comprise tails of varying length in some embodiments. Each channel can comprise an even number of tails in certain embodiments. Tails directly opposite one another around a channel can have the same length, and in some embodiments, tails directly opposite one another around a channel can have a different length. Tails adjacent to one another can have a different length in certain embodiments. The tails can be at an internal angle of about 89° to about 80° from the bottom surface of the distal barrier plate in some embodiments. The tails can be at an internal angle between 88-85°, 87-84°, 86-83° or 86-85° from the bottom surface of the distal barrier plate in some embodiments. The tails can be at an internal angle of about 87° from the bottom surface of the distal barrier plate in certain embodiments, and tails sometimes can be between 0.01 µm-2.0 mm in length. The tails can be between 0.05 µm-2.0 mm in length in certain embodiments. The tails around a channel are not in the channel in some embodiments. In certain embodiments, the housing can comprise (a) an actuator housing comprising a top portion, four sides, an inner surface, and a plurality of regularly spaced detent members disposed on at least one side of the housing, and (b) an alignment housing comprising an outside surface in contact with the inside surface of the actuator housing in a sliding arrangement, a plurality of regularly spaced detent members configured to releasably engage the detent members of the actuator housing and having a regular spacing that is substantially the same as the regular spacing of the detent members of the actuator housing, and a proximal opening having an inside surface configured to engage outer lateral sides of a loading block in certain embodiments. The housing can comprise a polymer material, and the polymer material of the housing can comprise molded polypropylene in some embodiments. The polymer material of the housing can comprise a thickness of about 0.005 inches to about 0.05 inches. The actuator housing can comprise a telescoping arrangement having multiple housing elements. The alignment housing can comprise a flange or a footing for the housing to rest in some embodiments. The actuator housing can comprise a member on the top portion of the actuator that maintains contact with and restricts lateral displacement of the proximal portion of the pipette tips in certain embodiments, where the member can be selected from the group consisting of foam, a raised grid, and a plurality of proximal alignment members in some embodiments. The device can comprise one or more arrays of 96, 384, 1356 or more pipette tips. A pipette tip unit can be arranged in an array of pipette tip units, and each pipette tip unit can comprise 2, 3, 4, 5, 6, 7, 8, 9, 10, 11, 12, 13, 14 or more nested pipette tips in some embodiments.

Also provided in some embodiments is a distal barrier plate that can be part of a pipette tip dispenser and is not in association with pipette tips, that comprises (a) a plurality of channels, where each channel comprises a diameter larger than the widest portion of a pipette tip; (b) a top surface; and (c) a bottom surface that comprises a plurality of tails around some or all of the channels, where: (i) the tails extend in a nearly perpendicular orientation from the bottom surface, and (ii) the tails around each channel contact a pipette tip when a pipette tip is dispensed and passes by the tails, thereby applying a frictional force on the pipette tip when it is dispensed. In some embodiments, the tails deflect outwards against the pipette tip before the pipette tip is dispensed, and/or at the same time the pipette tip is being dispensed (e.g., the pipette tip is translating), and sometimes the tails contact the proximal portion of a pipette tip. In some embodiments, a subset of channels in the distal barrier plate are surrounded by tails that eject pipette tips of an array at one time, and another subset of channels in the plate are surrounded by tails that eject pipette tips of the same array at another time. A distal barrier plate may include 2, 3, 4, 5, 6, 7, 8, 9, 10, 11, 12, 13, 14, 15, 16, 17, 18, 19 or 20 of such subsets of channels.

In some embodiments pertaining to a dispensing devices described in the preceding paragraph, the top surface and/or the bottom surface is substantial flat or planar. In certain embodiments, each channel can comprises 2, 3, 4, 5, 6, 7, 8, 9, 10 or more tails. Each channel of the barrier plate can comprise tails of the same length, and in some embodiments each channel of the barrier plate can comprise tails of different lengths. Channels located in the center of the barrier plate can comprise the longest tails. In certain embodiments, channels located in the center of the barrier plate can comprise the shortest tails. Subsequent channels concentrically disposed about a central longitudinal axis can comprise sequentially shorter tails in length in a stepwise manner. In certain embodiments, subsequent channels concentrically disposed about a central longitudinal axis can comprise sequentially longer tails in length in a stepwise manner. Channels located in the center of the barrier plate along the X axis can comprise tails of the same length and channels along the Y axis can comprise tails of varying length in certain embodiments. In some embodiments, channels located in the center of the barrier plate along the Y axis can comprise tails of the same length and channels along the X axis can comprise tails of varying length. Channels located in the center of the barrier plate along the X and Y axes can comprise tails of varying length in some embodiments. Each channel can comprise an even number of tails. Tails directly opposite one another around a channel can have the same length in some embodiments. In certain embodiments, tails directly opposite one another around a channel can have a different length. Tails adjacent to one another can have a different length in some embodiments. In certain embodiments, tails are at an internal angle of about 89° to about 80° from the bottom surface of the distal barrier plate. The tails can be at an internal angle between 88-85°, 87-84°, 86-83° or 86-85° from the bottom surface of the distal barrier plate in some embodiments. In certain embodiments, the tails can be at an internal angle of about 87° from the bottom surface of the distal barrier plate. The tails can be between 0.01 µm-2.0 mm in length, and sometimes the tails can be between 0.05 µm-2.0 mm in length. The tails around a channel are not in the channel in some embodiments.

Provided also in some embodiments is a method for simultaneously dispensing an array of pipette tips into a loading block, which comprises (a) providing a dispensing device that includes an array of regularly spaced pipette tips; (b) engaging the dispensing device with a loading block such that distal ends of pipette tips are disposed above or within receptacles of the loading block, the barrier plate comprising (i) a plurality of channels, where each channel has a diameter larger than the widest portion of a pipette tip; (ii) a top surface; and (iii) a bottom surface that comprises a plurality of tails around some or all of the channels, where the tails extend in a nearly perpendicular orientation from the bottom surface; and (c) actuating an actuator of the dispensing device so as to apply an axial force on the array of pipette tips, where the axial force dispenses the array of pipette tips through the channels and past the tails, whereby the tails contact the pipette tips and impart a frictional force on the pipette tips, thereby ejecting the array of pipette tips into respective receptacles in the loading block. In some embodiments, the tails deflect outwards against the pipette tip before the pipette tip is dispensed, and/or at the same time the pipette tip is being dispensed (e.g., the pipette tip is translating), and sometimes the tails contact the proximal portion of a pipette tip. In some embodiments, a subset of channels in the distal barrier plate are surrounded by tails that eject pipette tips of an array at one time, and another subset of channels in the plate are surrounded by tails that eject pipette tips of the same array at another time. A distal barrier plate may include 2, 3, 4, 5, 6, 7, 8, 9, 10, 11, 12, 13, 14, 15, 16, 17, 18, 19 or 20 of such subsets of channels.

In some embodiments pertaining to a dispensing device described in the preceding paragraph, the top surface and/or the bottom surface is substantial flat or planar. In certain embodiments, the barrier plate can comprise 2, 3, 4, 5, 6, 7, 8, 9, 10 or more tails. Each channel of the barrier plate can comprise tails of the same length. In some embodiments, each channel of the barrier plate can comprise tails of different lengths. Channels located in the center of the barrier plate can comprise the longest tails. In some embodiments, channels located in the center of the barrier plate can comprise the shortest tails. Subsequent channels concentrically disposed about a central longitudinal axis can comprise sequentially shorter tails in length in a stepwise manner in some embodiments. Subsequent channels concentrically disposed about a central longitudinal axis can comprise sequentially longer tails in length in a stepwise manner in certain embodiments. In some embodiments, channels located in the center of the barrier plate along the X axis can comprise tails of the same length and channels along the Y axis comprise tails of varying length. In some embodiments, channels located in the center of the barrier plate along the Y axis can comprise tails of the same length and channels along the X axis comprise tails of varying length. In certain embodiments, channels located in the center of the barrier plate along the X and Y axes can comprise tails of varying length. Each channel can comprise an even number of tails in some embodiments, and in certain embodiments tails directly opposite one another around a channel can have the same length. Tails directly opposite one another around a channel can have a different length in some embodiments, and in certain embodiments, tails adjacent to one another can have a different length. The tails can be at an internal angle of about 89° to about 80° from the bottom surface of the distal barrier plate in some embodiments. In certain embodiments, tails can be at an internal angle between 88-85°, 87-84°, 86-83° or 86-85° from the bottom surface of the distal barrier plate. In some embodiments, tails can be at an internal angle of about 87° from the bottom surface of the distal barrier plate. The tails can be between 0.01 μm-2.0 mm in length in some embodiments, and in certain embodiments, the tails can be between 0.05 μm-2.0 mm in length. The tails around a channel are not in the channel in some embodiments. The actuator can comprise an actuator housing and an alignment housing both having a clear polymer material to visualize ejection of the array of multiple pipette tips from the tails of the barrier member during actuation in some embodiments. The actuator housing can comprise a telescoping arrangement having multiple housing elements and where actuation of the actuator comprises collapsing the multiple housing elements from an extended state to a collapsed nested state in certain embodiments.

Certain embodiments are described in the following detailed description, claims and drawings.

BRIEF DESCRIPTION OF THE DRAWINGS

The drawings illustrate embodiments of the invention and are not limiting. For clarity and ease of illustration, the drawings are not made to scale and, in some instances, various aspects may be shown exaggerated or enlarged to facilitate an understanding of particular embodiments.

FIG. 2 shows an elevation view of an embodiment of a pipette tip.

FIG. 3 illustrates a cross section of the pipette tip of FIG. 2 taken along lines 3-3 of FIG. 2.

FIG. 7 shows an elevation view of an embodiment of a pipettor with a pipette tip engaged with a distal nozzle thereof.

FIG. 14A shows X and Y axes referenced herein.

DETAILED DESCRIPTION

Figure 1:
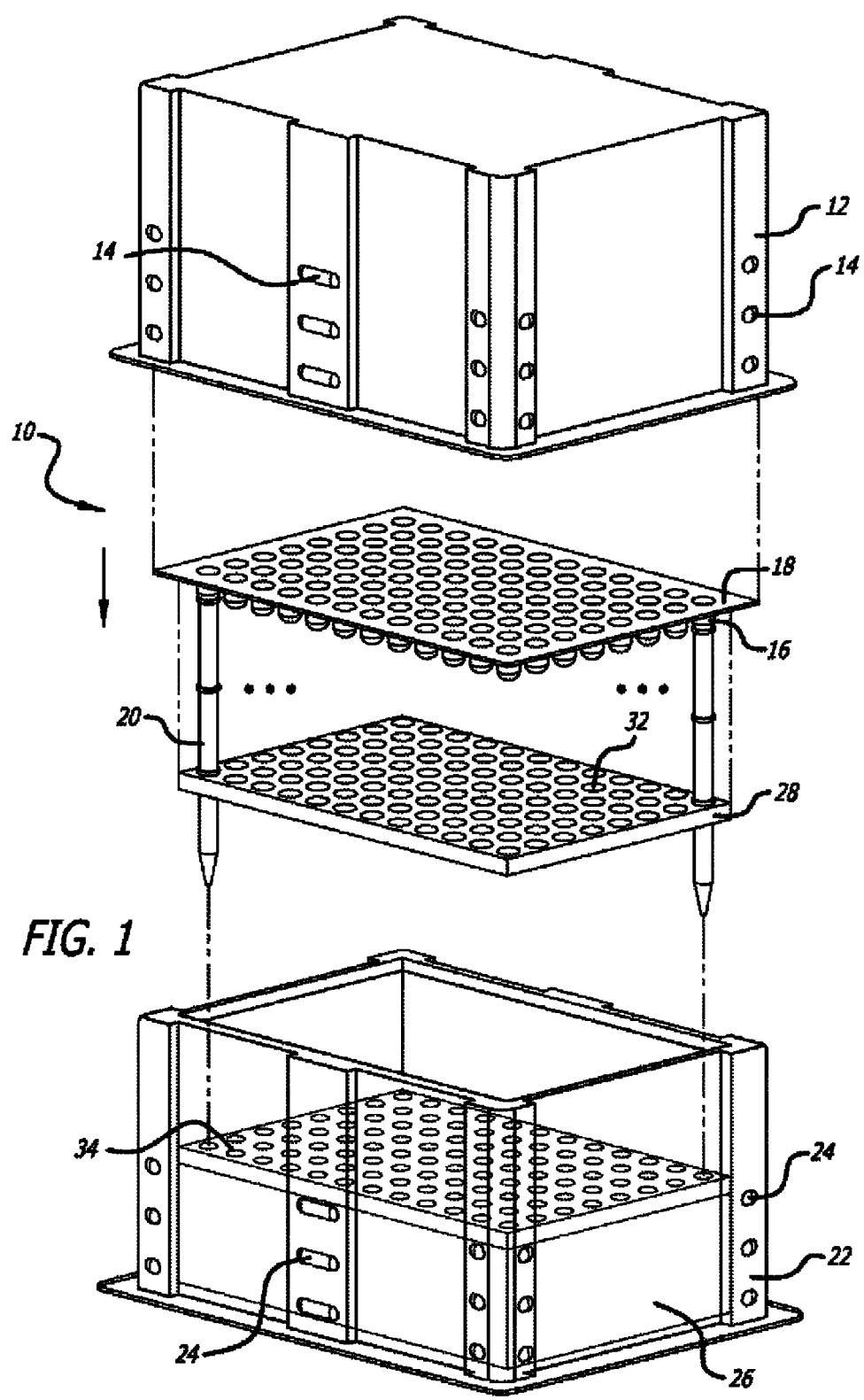
FIG. 1 shows an exploded perspective view of an embodiment of a pipette tip dispensing device.

Discussed herein are method and device embodiments for handling, storage and dispensing of pipette tips used for a variety of material handling applications. Pipette tips may generally be engaged with a distal nozzle of a pipettor or similar device in order to draw and drop liquid slugs in precise amounts. Such tips may be used for the transfer and handling of liquids for applications such as titration and dispensing of liquids, DNA sequencing, cycle sequencing, PCR and other DNA analysis as well as other liquid handling applications. For many of these applications, large numbers of samples must be processed in a precise manner and, as such, a large number of pipette tips are used for such methods. In order to avoid cross contamination of samples, pipette tips are typically used only once for each sample being processed. Because of the large number of samples being processed and the single use nature of the pipette tips, a large number of pipette tips need to engaged with pipettor type devices and then removed from those devices and disposed of.

Due to such large volume handling and disposal, it is desirable for some applications to have devices and methods for pipette tip transfer and loading in arrays of multiple tips from a single packaging source to avoid the need for disposing of a package for each array loaded onto a pipettor device. What is also desirable for some applications are devices and methods for loading an array of multiple pipette tips without the need to transfer a separate loading plate from the packaging of the tips which may cause additional waste for disposal in addition to affecting the cumulative z-axis height of the pipette tips being loaded. Some pipette tip dispensing device and method embodiments discussed herein are directed to the handling, storage and simultaneous dispensing of a plurality of pipette tips disposed in a regularly spaced array into a loading plate or block. Some of these embodiments have the capacity to serially dispense multiple arrays or pipette tips without transferring loading plates or the need for handling of individual pipette tips. Some embodiments of pipette tip dispensing devices discussed herein are also capable of dispensing arrays of multiple pipette tips accurately and conveniently without the need to transfer a loading tray from the packaging of the pipette tips.

Device and method embodiments described herein provide several advantages. Device and method embodiments herein allow for storing, loading or handling of pipette tips, and allow for convenient loading of pipette tips without the need to transfer a storage plate that may affect the z-axis location of the top surface of the loading block into which the pipette tips are transferred.

Device and method embodiments herein also allow for multiple pipette tips to be loaded simultaneously without the transfer of a storage plate. Such embodiments also allow for pipette tips to be stored in a nested configuration, in one or more nested column arrays for some embodiments, and allow the bottom pipette tip of each nested column to be conveniently dispensed into a loading plate or loading block.

A pipette tip can be of any geometry useful for dispensing fluids in combination with a dispensing device. Pipette tips sometimes are available in sizes that hold from 0 to 10 microliters, 0 to 20 microliters, 1 to 100 microliters, 1 to 200 microliters and from 1 to 1000 microliters, for example. The external appearance of pipette tips may differ, and certain pipette tips can have a continuous tapered wall forming a central channel or tube that is roughly circular in horizontal cross section, in some embodiments. A pipette tip can have any cross-sectional geometry that results in a tip that (i) provides suitable flow characteristics, and (ii) can be fitted to a dispenser (e.g., pipette), for example. Pipette tips sometimes taper from the widest point at the top-most portion of the pipette tip (pipette proximal end or end that engages a dispenser), to a narrow opening at the bottom most portion of the pipette tip (pipette distal end or end used to acquire or dispel fluid). In certain embodiments, a pipette tip wall includes two or more taper angles. The inner surface of the pipette tip sometimes forms a tapered continuous wall, in some embodiments, and in certain embodiments, the external wall may assume an appearance ranging from a continuous taper to a stepped taper or a combination of smooth taper with external protrusions. An advantage of an externally stepped taper is compatibility with pipette tip racks from different manufacturers. The bore of the top-most portion of the central channel or tube generally is wide enough to accept a particular dispenser apparatus (e.g., nozzle, barrel).

In some embodiments, a pipette tip has (i) an overall length of about 1.10 inches to about 3.50 inches (e.g., about 1.25, 1.50, 1.75, 2.00, 2.25, 2.50, 2.75, 3.00, 3.25 inches); (ii) a fluid-emitting distal section terminus having an inner diameter of about 0.01 inches to about 0.03 inches (e.g., about 0.015, 0.020, 0.025 inches) and an outer diameter of about 0.02 to about 0.7 inches (e.g., about 0.025, 0.03, 0.04, 0.05, 0.06 inches); and (iii) a dispenser-engaging proximal section terminus having an inner diameter of about 0.10 inches to about 0.40 inches (e.g., about 0.15, 0.20, 0.25, 0.30, 0.35 inches) and an outer diameter of about 0.15 to about 0.45 inches (e.g., about 0.20, 0.25, 0.30, 0.35, 0.45 inches). In the latter embodiments, the inner diameter is less than the outer diameter.

The wall of the distal section of a pipette tip sometimes is continuously tapered from the wider portion, which is in effective connection with the proximal section, to a narrower terminus. The wall of the distal section, in some embodiments, forms a stepped tapered surface. The angle of each taper in a distal section is between about zero degrees to about thirty degrees from the central longitudinal vertical axis of the pipette tip (e.g., about 0, 1, 2, 3, 4, 5, 6, 7, 8, 9, 10, 11, 12, 13, 14, 15, 16, 17, 18, 19, 20, 21, 22, 23, 24, 25, 26, 27, 28, 29 or 30 degrees), in certain embodiments. In some embodiments, the wall of the distal section forms stepped vertical sections. The wall thickness of a distal section may be constant along the length of the section, or may vary with the length of the section (e.g., the wall of the distal section closer to the proximal section of the pipette tip may be thicker or thinner than the wall closer to the distal section terminus; the thickness may continuously thicken of thin over the length of the wall). The distal section of a pipette tip generally terminates in an aperture through which fluid passes into or out of the distal portion. A distal section of a pipette tip may contain a filter, insert or other material.

The wall of the proximal section of a pipette tip sometimes is continuously tapered from the top portion, a narrower terminus. The top portion generally is open and often is shaped to receive a pipette tip engagement portion of a dispensing device. The wall of a proximal section, in some embodiments, forms a stepped tapered surface. The angle of each taper in the proximal section is between about zero degrees to about thirty degrees from the central longitudinal vertical axis of the pipette tip (e.g., about 0, 1, 2, 3, 4, 5, 6, 7, 8, 9, 10, 11, 12, 13, 14, 15, 16, 17, 18, 19, 20, 21, 22, 23, 24, 25, 26, 27, 28, 29 or 30 degrees), in certain embodiments. The wall thickness of a proximal section may be constant over the length of the section, or may vary with the length of the proximal section (e.g., the wall of the proximal section closer to the distal section of the pipette tip may be thicker or thinner than the wall closer to the top of the proximal section; the thickness may continuously thicken or thin over the length of the wall). A proximal section of a pipette tip may contain a filter, insert or other material.

In certain embodiments, pipette tips in a pipette tray comprise one or more of a filter component and/or an insert component. A filter may be located in any suitable portion of a pipette tip, and sometimes is located in a proximal portion of a pipette tip near a pipette tip aperture that can engage a dispensing device. A filter can be of any shape (e.g., plug, disk; U.S. Pat. Nos. 5,156,811 and 7,335,337) and can be manufactured from any material that impedes or blocks migration of aerosol through the pipette tip to the proximal section terminus, including without limitation, polyester, cork, plastic, silica, gels, and the like, and combinations thereof. In some embodiments a filter may be porous, non-porous, hydrophobic, hydrophilic or a combination thereof. A filter in some embodiments may include vertically oriented pores, and the pore size may be regular or irregular. Pores of a filter may include a material (e.g., granular material) that can expand and plug pores when contacted with aerosol (e.g., U.S. Pat. No. 5,156,811). In certain embodiments, a filter may include nominal, average or mean pore sizes of about 10, 9, 8, 7, 6, 5, 4, 3, 2, 1, 0.5, or 0.05 micrometers, for example. A section of a pipette tip also may include an insert or material that can interact with a molecule of interest, such as a biomolecule. The insert or material may be located in any suitable location for interaction with a molecule of interest, and sometimes is located in the distal section of a pipette tip (e.g., a material or a terminus of an insert may be located at or near the terminal aperture of the distal section). An insert may comprises one or more components that include, without limitation, multicapillaries (e.g., US 2007/0017870), fibers (e.g., randomly oriented or stacked, parallel orientation), and beads (e.g., silica gel, glass (e.g. controlled-pore glass (CPG)), nylon, Sephadex®, Sepharose®, cellulose, a metal surface (e.g. steel, gold, silver, aluminum, silicon and copper), a magnetic material, a plastic material (e.g., polyethylene, polypropylene, polyamide, polyester, polyvinylidenedifluoride (PVDF)), Wang resin, Merrifield resin or Dynabeads®). Beads may be sintered (e.g., sintered glass beads) or may be free (e.g., between one or two barriers (e.g., filter, frit)). Each insert may be coated or derivitized (e.g., covalently or non-covalently modified) with a molecule that can interact with (e.g., bind to) a molecule of interest (e.g., C18, nickel, affinity substrate).

FIG. 1 shows an exploded perspective view of an embodiment of a pipette tip dispensing device 10. The dispensing device embodiment 10 includes a displacement actuator that has an actuator housing 12 with a top portion, four sides, and an inner surface. Sets of regularly spaced detent members 14 are disposed on all four sides of the housing 12. Each set of detent members 14 on the actuator housing 12 includes three detent members 14 equally spaced in a vertical direction. A plurality of proximal alignment members 16 are disposed in a regularly spaced array of 8×12 alignment members 16 on an actuator plate 18 disposed at a top portion of the actuator housing 12. Each proximal alignment member 16 is configured to releasably engage and restrict the lateral displacement of a proximal end of a pipette tip, such as the pipette tip 20 illustrated in FIGS. 2 and 3.

An alignment housing 22 which is configured to slide within the actuator housing 12 includes an outside surface in contact with the inside surface of the actuator housing 12 in a sliding arrangement. The alignment housing 22 also includes a plurality of regularly spaced detent members 24 which are configured to releasably engage the corresponding detent members 14 of the actuator housing 12. As such, the detent members 24 of the alignment housing have a regular spacing that is substantially the same as the regular spacing of the detent members 14 of the actuator housing as shown by arrow 15 in FIG. 5A. Also, the detent members 24 of the alignment housing 22 have a shape that is configured to releasably engage the detent members 14 of the actuator housing. The alignment housing 22 has a rectangular proximal opening with an inside surface which is sized and configured to engage outer lateral sides of a loading block 26 which is shown disposed within the proximal opening of the alignment housing 22.

A distal barrier element in the form of a distal barrier plate 28 is disposed at a top portion of the alignment housing 22 and lies substantially parallel to the actuator plate 18 of the actuator. The distal barrier plate 28 includes a plurality of restrictive apertures 32 which are substantially aligned with corresponding respective proximal alignment members 16 of the actuator plate 18 within the actuator housing 12. The actuator housing 12 is configured to slide relative to the alignment housing 22 to a collapsed state where the proximal alignment members 16 directly engage the restrictive apertures 32 of the distal barrier plate 28 so as to push the last of a set of nested pipette tips through the barrier plate and into the respective channels 34 of the loading block 26 which is disposed below the barrier plate.

Figure 6A:
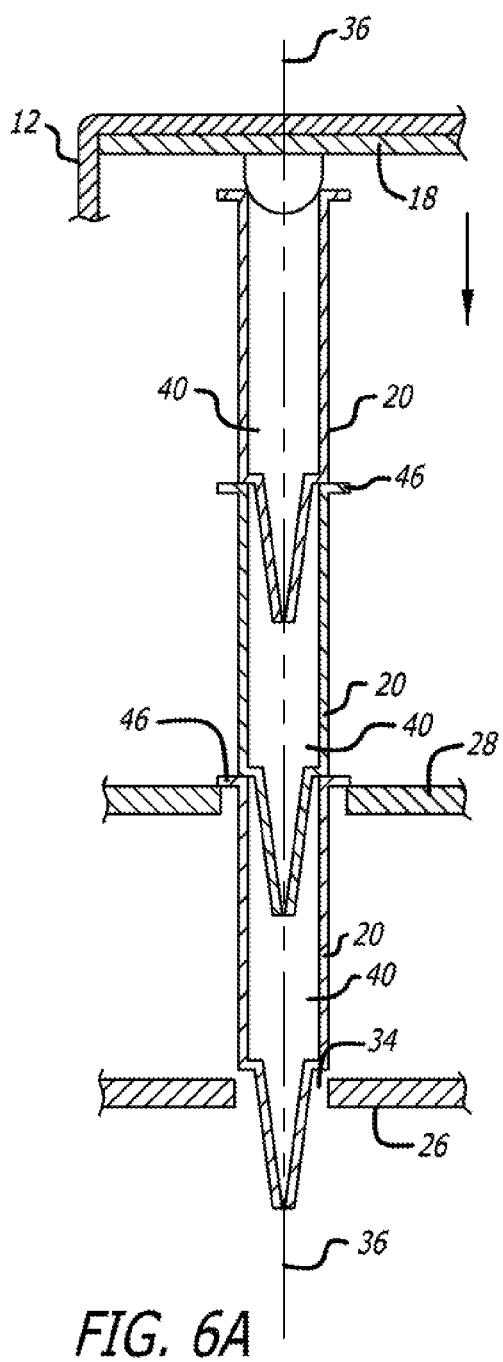
FIG. 6A shows an enlarged cut-away view in partial section of a stacked nested array of pipette tips engaged with a proximal alignment member, distal restrictive aperture and loading block prior to actuation.

In FIG. 1, a single column of nested pipette tips is shown disposed between a proximal alignment member 16 and distal restrictive aperture 32 for purposes of illustration, however, a column of nested pipette tips may generally be disposed between each proximal alignment member 16 and corresponding restrictive aperture 32. The longitudinal axis 36 of each of the pipette tips 20 in the nested array are substantially aligned and coaxial as shown in FIG. 6A. A shoulder portion 38 of the proximal most pipette tip is disposed against a proximal end of the adjacent pipette tip. During typical use, a column of an equal number of nested pipette tips 20 may be disposed between each of the respective proximal alignment members 16 and distal restrictive apertures 32 in a configuration that is the same as or similar to the configuration of nested tips shown. In addition, any desired number of columns could be used. The regular spacing of the proximal alignment members 16, distal restrictive apertures 32, and columns of nested pipette tips disposed therebetween may be about 1 mm to about 5 mm for some embodiments.

A specific embodiment of pipette tip 20 is shown in FIGS. 2 and 3, however, pipette tips may have a wide variety of configurations, dimensions and materials, each of which may be accommodated for use with any of the dispensing device embodiments discussed herein. For example, pipette tips may be configured as filter tips that include one, two, three or more filter elements disposed within a barrel of the tip in order to block aerosols from the pipettor device as well as other purposes.

The pipette tip 20 shown has a generally barrel shaped configuration which is concentrically disposed about a longitudinal axis 36 of the pipette tip 20. An inner lumen 40 extends coaxially along the length of the pipette tip 20 and tapers generally from the proximal opening of the pipette tip to a smaller distal opening. The proximal opening at a proximal end 42 of the tip 20 may have an inside surface with a tapered contour that is configured to engage an outer surface of a distal nozzle of a pipettor device, such as the pipettor device 44 shown in FIG. 7, in a sealed and releasable arrangement.

An outer surface of the proximal end of the pipette tip may have a rim, shoulder or other structure 46 that forms a major outer transverse dimension of the tip 20 which is disposed at the axial position of the pipette tip 20 having the largest transverse dimension. The barrel shaped configuration may have a generally round transverse cross section with the major outer transverse dimension at the proximal end 42 of the pipette tip of about 0.2 inches to about 0.4 inches, more specifically, about 0.25 inches to about 0.35 inches, for some embodiments. The outer transverse dimension of the pipette tip may taper to a minor outer transverse dimension at a distal end of the pipette tip 20 of about 0.02 inches to about 0.05 inches, more specifically, about 0.03 inches to about 0.04 inches, for some embodiments. The inner lumen may have a contour and taper that substantially corresponds to the taper and contour profile of the outer surface. The distal port or opening at the distal end of the inner lumen of the pipette tip may have a transverse dimension or diameter of about 0.01 inches to about 0.03 inches, more specifically, about 0.015 inches to about 0.025 inches, for some embodiments.

The shoulder portions 38 of the outer surface of some pipette tip embodiments 20 may have a minor transverse dimension that will fit within the proximal opening of another similar pipette tip and a major transverse dimension that is larger than the proximal opening of a similar pipette tip. With such an arrangement, the shoulder portion 38 of a first pipette tip thereby includes a distal surface or feature that may engage a proximal end or surface of another corresponding second pipette tip that is in nested engagement with the first pipette tip. The engagement of the shoulder portion of the first pipette tip with a proximal surface of the second pipette tip allows the transfer axial force between the first and second nested pipette tips without engaging the respective inner and outer tapered surfaces of the tips which might cause them to bind together making release of the tips from each other difficult.

The wall thickness of some embodiments of pipette tips may be about 0.003 inches to about 0.01 inches and the overall length of some pipette tip embodiments may be about 1.5 inches to about 3.5 inches, more specifically, about 2 inches to about 3 inches. Some embodiments of pipette tips may be made of suitable polymers such as polypropylene, polyethylene, polystyrene, polyurethane and the like as well as any other suitable polymers. Such polymer materials as well as others may be configured to allow the proximal end or portion of the pipette tip to elastically deform or compress sufficiently to allow passage through the restrictive aperture 32 of the barrier member 28 if sufficient threshold axial force is applied to a pipette tip 20 engaged with a restrictive aperture 32. For such embodiments, once the pipette tip 20 has passed through the restrictive aperture 32, and the inward radial constraint of the restrictive aperture on the pipette tip has been removed, the proximal end or portion elastically returns to its original shape. Such a process may occur with any structure 46 that forms the major outer transverse dimension of the pipette tip 20.

Figure 4:
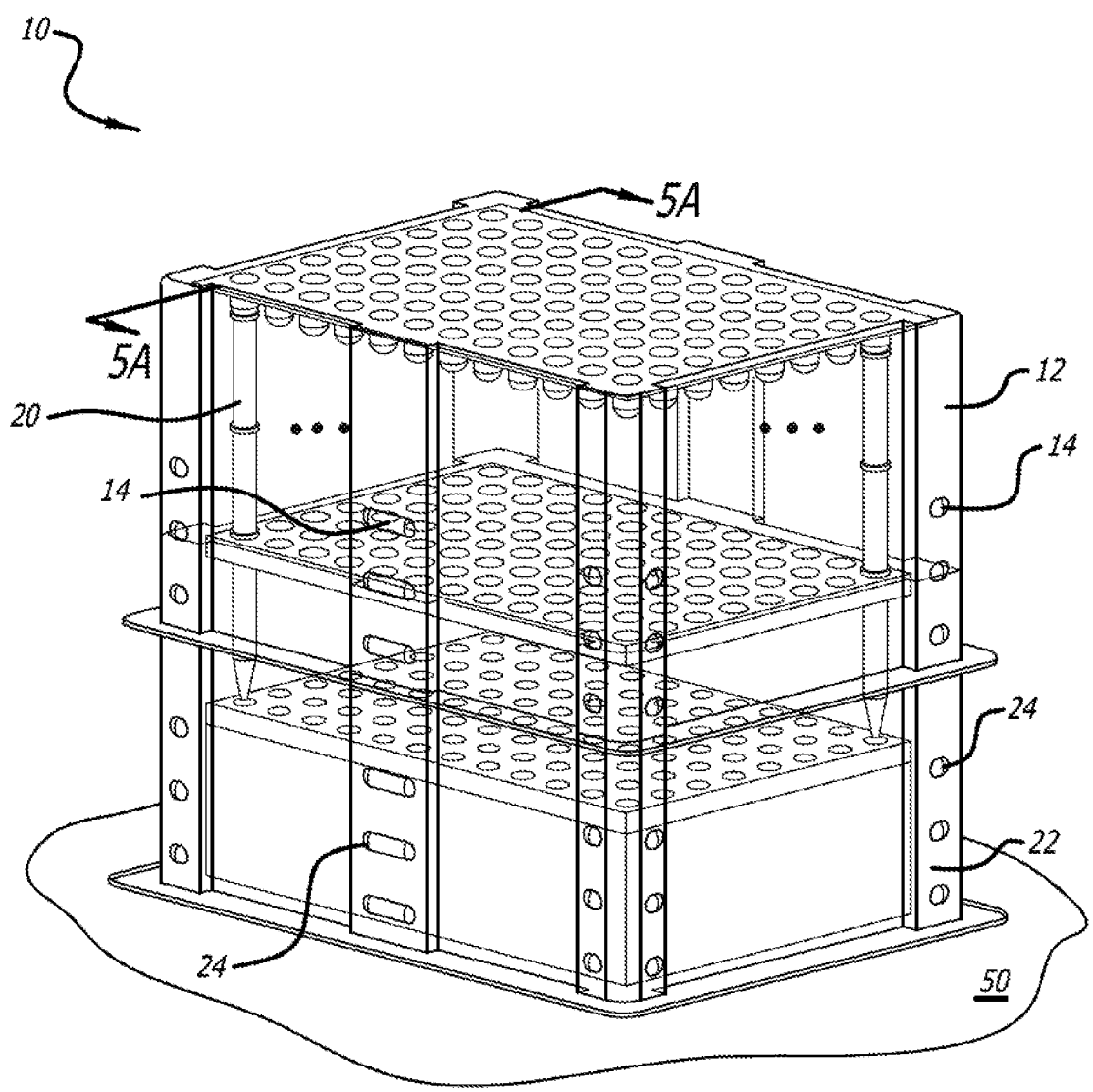
FIG. 4 shows a perspective view of the pipette tip dispensing device of FIG. 1.

Referring again to FIG. 1 as well as FIGS. 4-6, the pipette tip dispensing device 10 is shown in more detail. The displacement actuator includes the actuator housing 12 that may be made from a clear, thin rigid material formed into a substantially rectangular configuration with an open bottom portion, substantially planar sides that may be arranged substantially perpendicular to each other and to the top surface and actuator plate 18 disposed within an upper end of the housing 12. For some embodiments, the actuator housing 12 may be made from a thin clear polymer material that is transparent or translucent and may have a thickness of about 0.005 inches to about 0.05 inches. For some embodiments, the actuator housing 12 may be made from suitable metals, such as aluminum, or polymers such as polypropylene, polycarbonate, polyethylene, polystyrene, polyurethane and the like as well as any other suitable polymers that may be molded, thermoformed or the like. The housing 12 may have a thickness that allows for some flexibility or elastic deformation of the sides or proximal surface upon manual manipulation but provides sufficient structural strength to maintain its general shape upon manual manipulation and actuation. The actuator housing 12 is also sufficiently rigid to be self-supporting and maintains integrity sufficient to apply actuation force on the actuator plate 18 and the array of pipette tips 20 being dispensed through the restrictive apertures 32 of the barrier plate 28.

The proximal actuator plate 18 has a plurality of proximal alignment members 16 disposed substantially in a plane in a regularly spaced array and each proximal alignment member 16 is configured to releasably engage and restrict lateral displacement of a proximal end of a pipette tip 20 that is engaged with the alignment member 16. The proximal alignment members 16 may be cone shaped abutments extending from a distal surface of the actuator plate 18 that may be configured to engage or fit within the proximal port of corresponding pipette tips to be used with the proximal actuator plate 18. The proximal actuator plate 18 may be made from suitable metals, such as aluminum, or polymers such as polypropylene, polycarbonate, polyethylene, polystyrene, polyurethane and the like as well as any other suitable polymers that may be molded, thermoformed or the like. The proximal actuator plate 18 and proximal alignment members 16 may be molded from a monolithic structure of the same material for some embodiments. The proximal actuator plate 18 may have a thickness of about 0.05 inches and about 0.25 inches. The proximal actuator plate 18 may be secured to an inner proximal surface of the actuator housing and may be configured with sufficient rigidity to maintain a generally planar configuration when applying axial force to an array of pipette tips 20 engaged with the proximal members 16 thereof as the pipette tips are being pushed through the restrictive apertures 32 of the distal barrier plate 28. For some embodiments, the proximal actuator plate may be integrally molded or otherwise formed with the actuator housing 12. Some pipette tip array embodiments of the actuator plate 18 and barrier member may include 96 pipette tip arrays of 8×12 pipette tips spaced about 9 mm apart center to center, some other embodiments may include 384 pipette tip arrays of 16×24 pipette tips spaced about 4.5 mm apart center to center. Other pipette tip array embodiments may include more or less pipettes depending on the application.

The alignment housing assembly includes a substantially rectangular structure having an outside surface which is configured to slidingly engage the inside surface of the actuator housing 12. The alignment housing embodiment 22 shown has four sides formed from a clear, thin, substantially rigid material that may be transparent or translucent in order to allow an operator to visualize a pipette tip loading process. The four sides of the alignment housing 22 include the regularly spaced detent members 24 which are configured to releasably engage the corresponding detent members 14 of the actuator housing 12. The detent members 24 have a regular vertical spacing that is substantially the same as the regular vertical spacing of the detent members of the actuator housing. The engagement of corresponding detent members secures the actuator housing 12 in fixed relation to the alignment housing until a threshold force applied to one of the housings relative to the other overcomes the detent engagement. The detent engagement may be used to facilitate incremental movement between the housings while maintaining the housings in a mechanically coupled relation when not in use, during shipment while loaded with nested arrays of pipette tips or at any other suitable time. The amount of engagement of the corresponding detent members may be about 0.005 inches to about 0.05 inches for some embodiments. The angle that the sides of the alignment housing 22 form with the barrier plate 28 may be the same as or similar to the angle the sides of the actuator housing 12 form with the actuator plate 18. These similar angles may be configured to facilitate the sliding or telescoping movement between the inside surface of the sides of the actuator housing 12 and the outer surface of the sides of the alignment housing 22.

The alignment housing 22 may be made from the same thin clear polymer material as that of the actuator housing 12 and have a similar dimensional configuration such as a thickness of about 0.005 inches to about 0.05 inches. For some embodiments, the alignment housing may be made from suitable metals, such as aluminum, or polymers such as polypropylene, polycarbonate, polyethylene, polystyrene, polyurethane and the like as well as any other suitable polymers that may be molded, thermoformed or the like. The alignment housing 22 may have a thickness that allows for some flexibility or elastic deformation of the sides or proximal surface upon manual manipulation but provides sufficient structural strength to maintain its general shape upon manual manipulation and actuation and may be self-supporting. In particular, the alignment housing 22 maintains integrity sufficient to resist actuation force on an array of pipette tips being dispensed through the restrictive barrier plate 28 at the top or proximal end of the alignment housing 22.

The alignment housing 22 includes a proximal opening 48 which has an inside surface or flange that is configured to engage an outside surface perimeter of the loading block 26. For some embodiments, the proximal opening 48 of the alignment housing may be covered with a thin material, such as a thin polymer material (not shown) for storage and shipment of the device. Such a cover material may be configured to be temporarily secured to the alignment housing with a peelable adhesive bond such that the cover material may be peeled off just prior to use with a tab or other extension that a user may grasp. The cover material may be useful for maintaining the stacked array of pipette tips contained within the device during shipment as well as preventing contamination of contained pipette tips.

In some embodiments, the inside transverse dimensions of the proximal opening 48 of the alignment housing 22 should be a close fit with not more than about a 0.005 inch to about a 0.05 inch gap between the outside surface of the perimeter of the loading block 26 to be used and the inside surface of the proximal opening 48. This controlled fit may be used to assure that the restrictive apertures 32 of the barrier plate 28 are properly aligned with the channels 34 of the loading block 26. It may generally be undesirable for the outer surface perimeter of the loading block 26 to have snug fit with the inside surface of the alignment housing 22 as this might make removal of the pipette tip dispensing device from the loading block 26 difficult.

The substantially planar barrier element in the form of the barrier plate 28 is disposed at a top portion of the alignment housing 22 substantially perpendicular to the sides of the alignment housing and substantially parallel to the actuator plate 18 of the actuator. The barrier plate 28 includes a plurality of the restrictive apertures 32 in an array which is substantially aligned with respective proximal alignment members 16 of the actuator plate 18. The restrictive apertures 32 are configured to engage an outside surface of a pipette tip, restrict lateral displacement of a pipette tip and resist axial displacement of the pipette tip until an axial threshold force is imparted to the pipette tip. Once the threshold axial force is reached, a pipette tip 20 may pass through the restrictive aperture and be ejected into the corresponding loading channel 34 of the loading block 26 disposed below the restrictive aperture 32. As soon as the major transverse dimension of the pipette tip 20 clears the barrier plate 28, gravitational force on the pipette tip 20 moves the tip 20 into the channel 34 in a distal or downward direction until the major transverse dimension or proximal end of the pipette tip registers on the edge of the channel 34 in the loading block 26.

The barrier plate 28 may be secured around its perimeter to an upper edge or rim of the alignment housing by welding, adhesive bonding or any other suitable method. The barrier plate 28 may have a thickness and material rigidity sufficient to prevent significant deformation upon the application of actuation force to the pipette tips 20 disposed in the plate 28. As such, the barrier plate 28 may have a thickness of about 0.05 inches to about 0.3 inches, more specifically, about 0.1 inches to about 0.25 inches. For some embodiments, the barrier plate 28 may be made from suitable metal, such as aluminum, or polymers such as polypropylene, polycarbonate, polyethylene, polystyrene, polyurethane and the like as well as any other suitable polymers that may be molded, thermoformed or the like. For some embodiments, the barrier plate 28 may have a length of about 2 inches to about 6 inches and a width of about 1 inch to about 3 inches.

For some embodiments, the restrictive apertures 32 of the barrier plate 28 include holes through the barrier plate 28 that may have an inner transverse dimension sized and configured to have a mechanical fit or engagement having an interference fit with the major outer transverse dimension 46 of the pipette tips 20 that are to be used with the device. The spacing of the array of restrictive apertures 32 may generally be configured to match the spacing and configuration of the alignment members 16 of the actuator plate 18, which may also match the configuration of the array of channels 34 in a suitable loading block 26. Such an interference fit requires that the restrictive aperture 32 have an inner transverse dimension or diameter that is less than the major outer transverse dimension 46 of the pipette tips.

This interference fit may be overcome by the application of a threshold axial force on a pipette tip 20 which is engaged with the restrictive aperture 32. For some embodiments, the interference fit is overcome by elastic deformation, deflection or compression of the proximal end or major transverse dimension portion 46 of the pipette tip 20 as it is forced through the restrictive aperture 32. The more interference in the fit and the harder the shore hardness of the material of the pipette tip 20, the greater the threshold force required to push the pipette tip 20 through the restrictive apertures 32. For some embodiments, this interference fit may have an interference of up to about 0.003 inches, more specifically, up to about 0.002 inches. For some embodiments, the restrictive apertures 32 of the barrier plate 28 may have an inner transverse dimension or diameter of about 1 mm to about 9.1 mm. The restrictive apertures 32 of the barrier plate 28 may have substantially parallel sides, be configured with tapered sides, have chamfered edges or edges with a radius or any other suitable configuration.

Figure 5A:
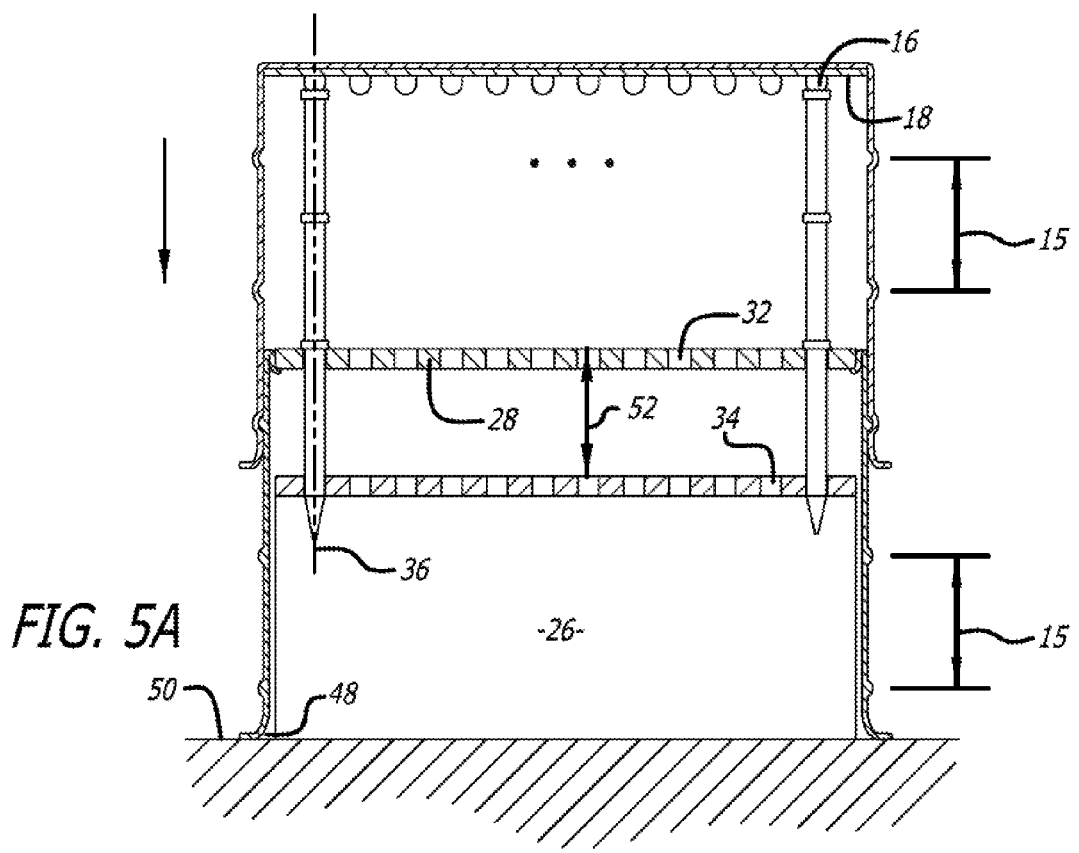
FIG. 5A is a transverse cross section of the dispensing device of FIG. 4 taken along lines 5A-5A of FIG. 4, showing a single column of three nested pipette tips disposed between a proximal alignment member of the actuator plate and a respective restrictive aperture of the barrier plate.

Vertical spacing between the top of the barrier plate 28 and the top of the loading block 26, as shown by arrow 52 in FIG. 5A, may be configured such that a distal end or distal portion of a pipette tip 20 which is engaged with a restrictive aperture of the barrier plate 28 is disposed within a hole or channel 34 of a loading block 26 so long as that loading block is engaged with the alignment housing 22. In this arrangement, the pipette tips are preloaded into the holes or channels 34 of the loading block 26. After being ejected from the barrier plate 28 once a threshold axial force has been applied them, they will continue down into the channels 34 of the loading block 26. Such distal tip engagement of the pipette tips into the channels 34 of the loading block 26 reduces or prevents potential jams or mis-feeds of the pipette tips after ejection from the restrictive apertures 32 of the barrier plate 28.

Figure 5B:
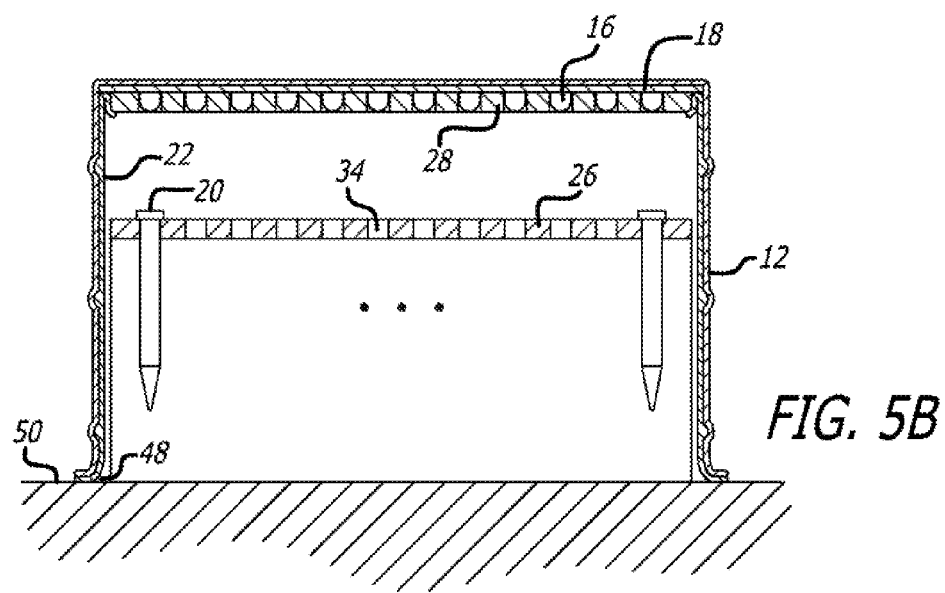
FIG. 5B shows the view of FIG. 5A after the actuator has been fully actuated three clicks to a position where all nested pipette tips have been ejected into loading blocks and the proximal alignment members are disposed within respective distal restrictive apertures.

For some embodiments, the vertical distance between the bottom of the barrier plate 28 and the bottom of the alignment housing 22 as well as the vertical spacing between the proximal actuator plate 18 and the bottom of the actuator housing 12 may be important. In particular, for some embodiments, these distances may be selected or otherwise configured such that the actuator housing 12 may be depressed down far enough to allow the last array of pipette tips 20 engaged directly with the proximal alignment members 16 of the proximal alignment plate 18 to be forced through the barrier plate 28 and into a loading block 26, as shown in FIG. 5B before the bottom of the actuator housing 12 contacts the working surface 50 upon which the loading block 26 and alignment housing 22 are disposed.

In use, an array of multiple pipette tips 20 may be dispensed into a loading block 26, with the pipette tip dispensing device embodiments discussed herein. For some embodiments, the dispensing device 10 is provided loaded with a regularly spaced array of 8×12 columns of pipette tips nested with 3 pipette tips in each column as shown in FIG. 5A and in more detail in FIG. 6A. The nested, regularly spaced array may be disposed between any or all of the respective proximal alignment members 16 and corresponding restrictive apertures 32 with a longitudinal axis 36 of each nested column of pipette tips being substantially aligned and coaxial with the respective proximal alignment members 16 and restrictive apertures 32. The proximal opening 48 of the alignment housing 22 may then be placed over and engaged with a loading block 26 such that distal ends of the distal most pipette tips 20 of each column, which are engaged with restrictive apertures of the barrier member 28, are disposed within channels 34 of the loading block 26 again as shown in FIG. 6A. Also, the outer perimeter surface of the loading block 26 is engaged with or otherwise laterally constrained by the inner surface of the alignment housing 22 to prevent substantial relative lateral movement between the loading block 26 and the alignment housing 22. Once the dispensing device 10 is so engaged with the loading block 26, the actuator may be actuated so as to apply an axial force on the array of columns of pipette tips 20 engaged with the restrictive apertures 32.

Figure 6B:
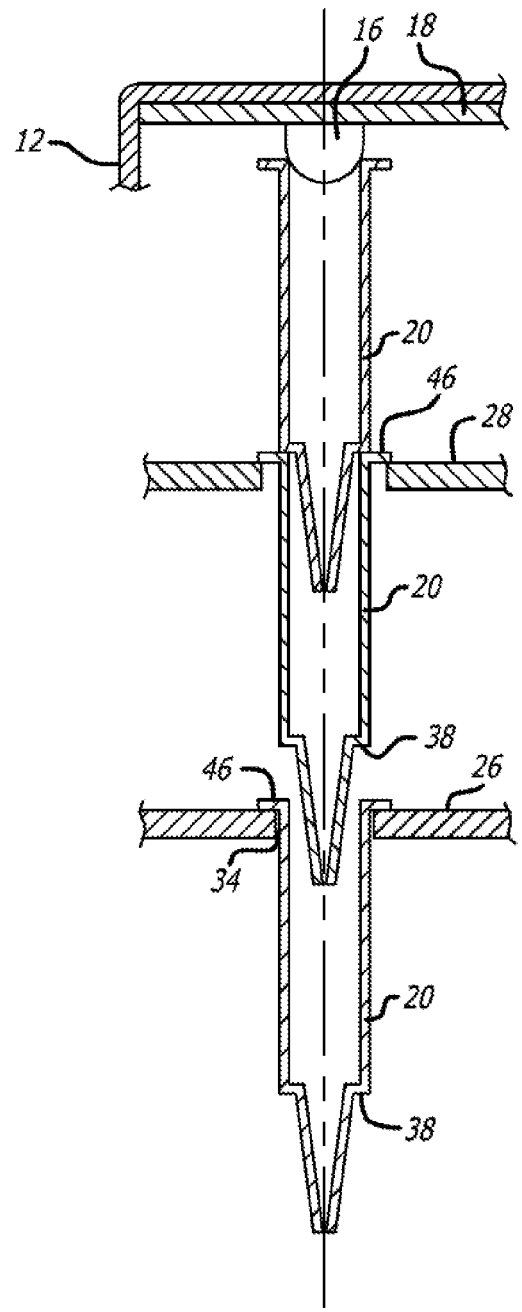
FIG. 6B shows the same view as FIG. 6A after the actuator has been advanced or actuated one click so as to move the actuator plate towards the barrier plate and eject the distal most pipette tip of the nested column into the corresponding aperture of the loading block.

For some embodiments, the axial force of the actuation may be generated by manually applying a downward force on an upper outside surface of the actuator housing 12. The force on the actuator housing 12 is then transferred to the actuator plate 18 and proximal alignment members 16 thereof, which, in turn, transmits the axial force to the nested columns of pipette tips 20. The manually applied force on the actuator housing 12 is continued until a threshold axial force is achieved so as to deform the major transverse portions 46 of the pipette tips 20 engaged with the restrictive apertures 32 of the barrier plate 28. As the force is applied, the proximal portions and major transverse dimension portions 46 of the pipette tips 20 may be elastically deformed and forced through the restrictive apertures 32 so as to eject the row or array of pipette tips engaged with the restrictive apertures into respective channels 34 in the loading block 26 as shown in FIG. 6B with the proximal major transverse dimension portion 46 of the pipette tips engaging the top surface of the channels 34 of the loading block 26.

Once the distal most array of pipette tips 20 are dispensed into the loading channels 34 of the loading block 26, the next row of pipette tips 20 move down into the restrictive apertures 32 of the barrier plate 28 and come to a stop as the major transverse dimension portions 46 of those pipette tips 20 engage the restrictive apertures 32. The downward progress of the actuator housing 12 and actuator plate 18 is also resisted by the engagement of corresponding detent members of the actuator housing 12 and alignment housing 22 at the end of the actuation stroke or step. The dispensing device 10 may then be lifted from the fully loaded loading block 26 so as to expose the newly loaded pipette tips 20. In addition, the loading block 26 may then be transferred to another location for use of the newly loaded pipette tips 20.

For dispensing device embodiments having the array of nested columns of pipette tips disposed therein, this process may be repeated by re-engaging the alignment housing 22 with empty loading blocks 26 at the beginning of each loading cycle and the actuator depressed so as to load a new set of pipette tips 20 into the empty block. As the last array of pipette tips 20 are ejected from the barrier plate 28, the proximal alignment elements 16 may be configured to engage and enter the restrictive apertures 32 of the barrier plate 28 so as to assure ejection of the final row of pipette tips 20 from the barrier plate.

During the dispensing process, if the actuator housing 12 and alignment housing 22 comprise a clear or translucent material, such as a clear or translucent polymer material, the ejection of the array of multiple pipette tips 20 from the restrictive apertures 32 of the barrier member 28 may be visualized during actuation. For manually actuated processes, the alignment housing 22 of the device 10 may be manually placed over and engaged with loading blocks 26 as needed. The pipette tip dispensing device 10 may also be manipulated by a robotic positioning device (not shown) such as a three axis to six axis robotic positioning device that may be configured to engage the alignment housing 22 with an empty loading block 22, actuate the actuator of the dispensing device 10, remove the dispensing device 10 from the loading block 26 that is newly loaded with pipette tips 20, remove the loaded loading block 26 and replace it with an empty loading block 26 and repeating the process.

Figure 8:
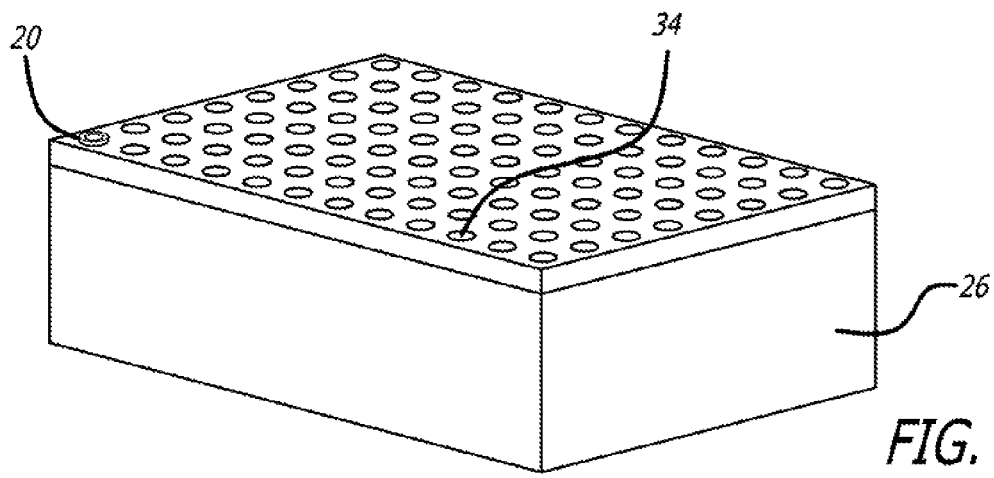
FIG. 8 is a perspective view of an embodiment of a loading block.
Figure 9:
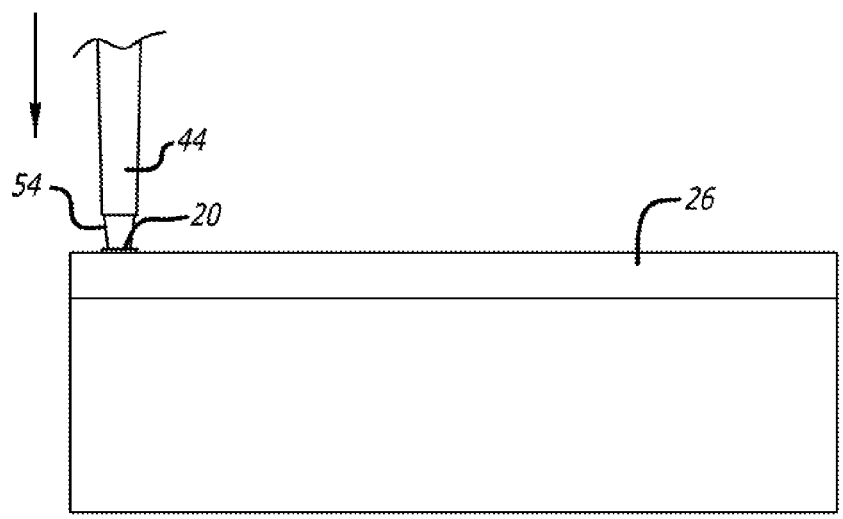
FIG. 9 shows a distal nozzle of a pipettor engaging a proximal port of a pipette tip disposed in a loading block.

Once the pipette tips 20 are loaded into the loading block 26 as shown, the pipette tips 20 may then be engaged with a pipettor device, such as pipettor device 44. FIGS. 8 and 9 show a loading block 26 with a pipette tip 20 disposed in a loading channel 34 of the block 26 and a nozzle 54 of a pipettor 44, such as the pipettor 44 of FIG. 7, engaged with the proximal port of the pipette tip 20. When the pipettor nozzle 54 is engaged with the proximal port of the pipette tip 20, the pipettor 44 may then be used for any of the applications discussed herein as well as any other suitable applications. Once the pipette tip 20 on the pipettor device 44 has been used, it may be ejected from the pipettor device 44 and replaced with a new pipette tip 20 from the loading block 26 and the process repeated.

Figure 10:
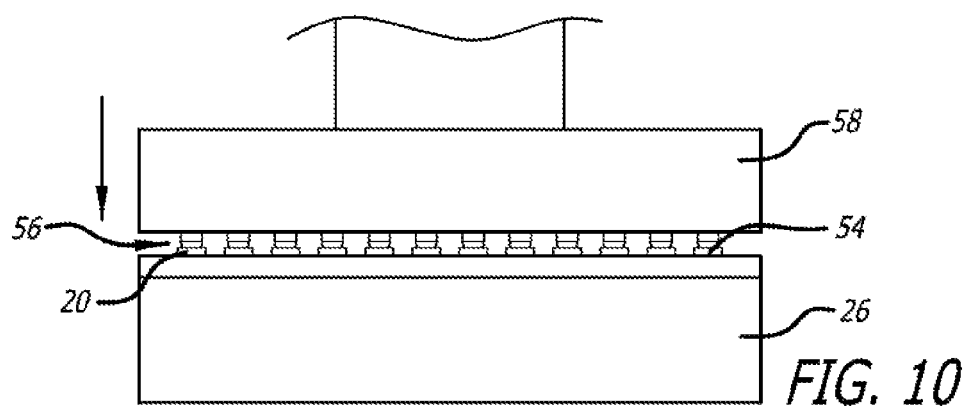
FIG. 10 shows multiple nozzles of an automated manifold engaging multiple corresponding pipette tips disposed in a loading block.

For automated method embodiments, an array 56 of multiple nozzles 54 of a robotic or automated pipettor device 58 may be engaged simultaneously with an array of pipette tips 20 as shown in FIG. 10. Such a loading block 26 may be loaded with the array of pipette tips 20 with the dispensing device 10 of FIG. 1. Once the pipette tips 20 disposed on the automated pipettor device 58 have been used for the intended application, they may be ejected from the pipettor device 58 and disposed of. A new set of pipette tips 20 may then be loaded onto the nozzles 54 pipettor device 58 from a freshly filled loading block 26 which has been filled by dispensing device 10. Such an automated process is facilitated by the use of the pipette tip dispensing device 10 or other similar embodiments as the loading blocks 26 may be quickly and conveniently refilled with a new array of pipette tips 20 without the need to transfer a loading plate or tray from the pipette tip packaging.

Figure 11:
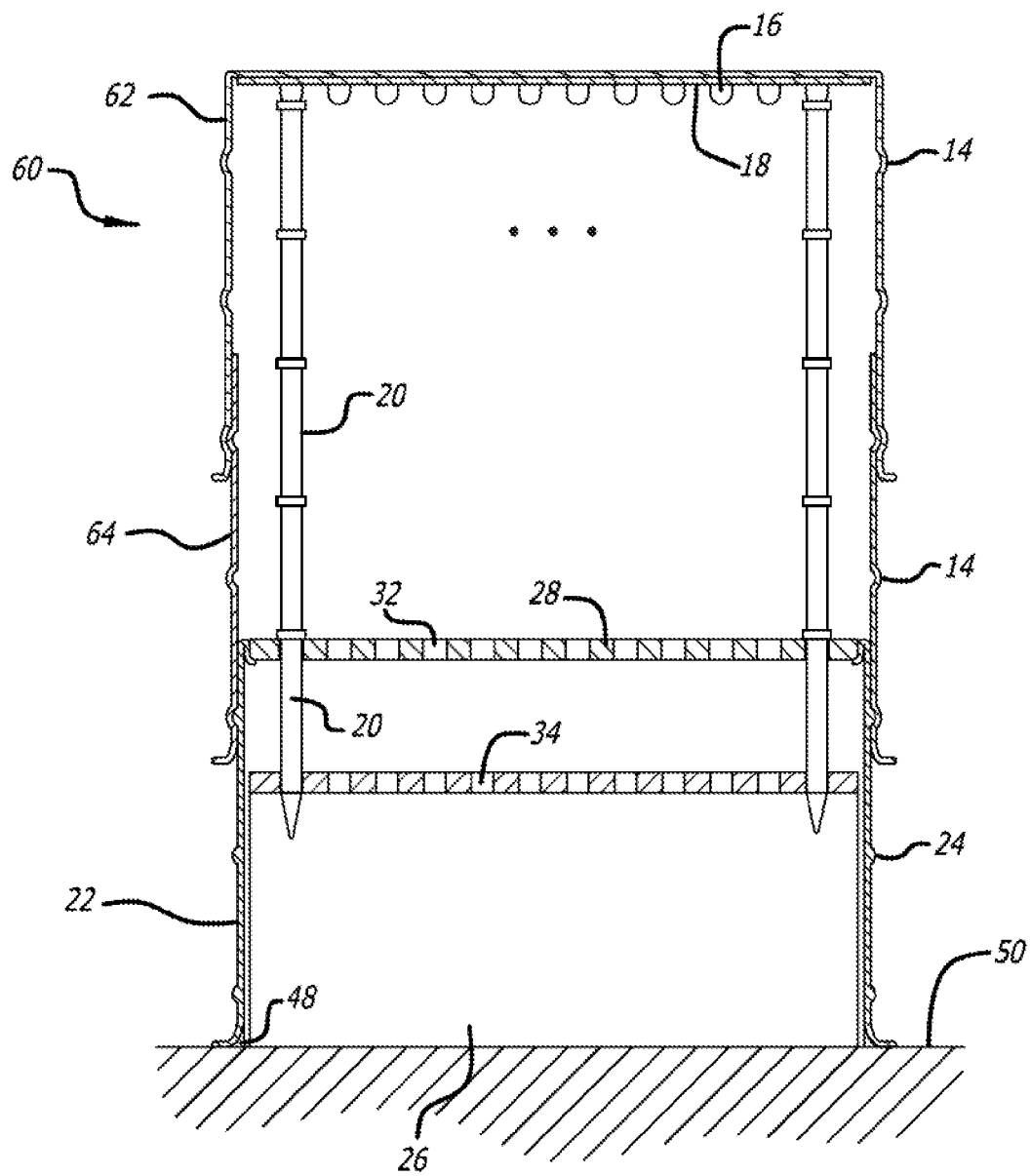
FIG. 11 shows an elevation view in transverse cross section of a telescoping embodiment of a pipette tip dispensing device with the actuator housing assembly in a fully extended state and a full column of nested pipette tips disposed between the barrier plate and proximal alignment members.
Figure 12:
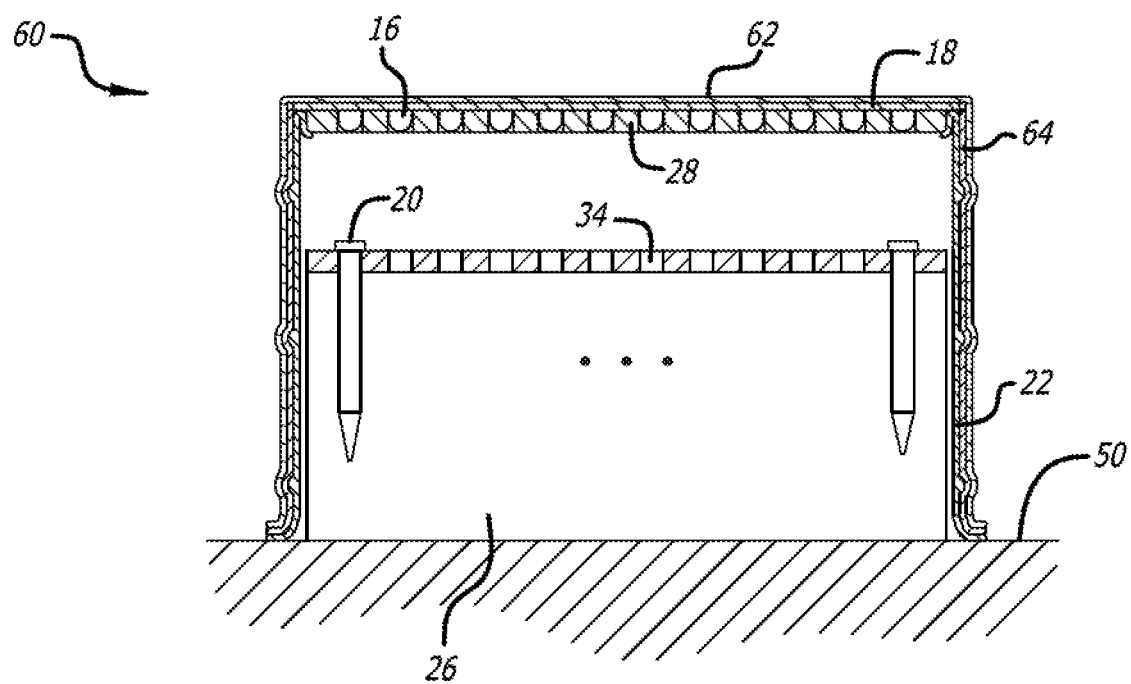
FIG. 12 shows the pipette tip dispensing device of FIG. 11 in a compressed state with the telescoping elements of the actuator housing in a collapsed state.

FIGS. 11 and 12 illustrate an embodiment of a pipette tip dispensing device similar in many respects to the dispensing device embodiment 10 of FIG. 1, except that the actuator housing of the embodiment includes a telescoping configuration that allows for the storage and dispensing of a greater amount of nested pipette tips disposed in a regularly spaced array. The dispensing device 60 of FIGS. 11 and 12 includes an alignment housing 22 that may have features, dimensions and materials that are the same as or similar to those of the alignment housing 22 of FIG. 1, including the details of the barrier plate 28 and proximal opening 48 which may be configured to engage a loading block 26 in the same manner as the proximal opening 48 discussed above. The proximal opening or port 48 may also include a polymer peelable cover sheet over the proximal port such as the cover discussed above. The telescoping nature of the actuator housing, however, may be configured to allow a greater number of pipette tips 20 to be disposed in a nested stacked array between the respective proximal alignment members 16 and restrictive apertures 32 of the barrier plate 28.

The particular embodiment of the dispensing device 60 shown in FIG. 1 is shown with 3 nested, stacked pipette tips 20 and the embodiment of FIG. 11 is shown accommodating 5 nested, stacked pipette tips 20 when in an extended state. Although these embodiments are shown to accommodate arrays of 3 and 5 nested pipette tips, the respective devices 10 and 60 may also be configured to accommodate a different number of nested pipette tips depending the housing configurations and dimension of the pipette tips 20 being used. Arrays of nested pipette tips stacked from about 2 pipette tips per stack to about 30 pipette tips per stack may be used, more specifically, about 3 pipette tips per stack to about 20 pipette tips per stack, and even more specifically, about 4 pipette tips to about 10 pipette tips, may be used.

The actuator housing includes a proximal housing member 62 and a distal housing member 64 that is vertically displaceable within the proximal housing member 62. The distal housing member 64 has no top portion and has an inside surface configured to slidingly engage the outer lateral surfaces of the alignment housing 22 in a manner similar to the engagement between the alignment housing 22 and actuator housing 12 discussed above. FIG. 12 illustrates the pipette tip dispensing device 60 of FIG. 11 in a collapsed state with all pipette tips 20 having been dispensed from the device and the proximal alignment members 16 of the proximal actuator housing 62 engaged with the respective restrictive apertures 32 of the distal barrier plate 28. The detent members 14 and 24 of the proximal actuator housing 62, distal actuator housing 64 and alignment housing 22 are also engaged in this collapsed state. The construction of the proximal actuator housing member 62 and distal actuator housing member may have the same or similar features, dimensions and materials as those of the actuator housing 12 and alignment housing 22 discussed above for some embodiments.

A pipette tip unit is arranged in an array of pipette tip units in some embodiments. Each unit has a plurality of nested pipette tips, and units are arranged in an array in certain embodiments. The relative configuration of nested pipette tips often is determined where a first portion of an inner surface of a first pipette tip interferes with a second portion of the outer surface of a second pipette tip nesting in and above the first pipette tip (e.g., the inner diameter of the first portion is about equal to the outer diameter of the second portion). Pipette tips can be dispensed as an array of pipette tips one pipette tip (i.e., one level) high. For example, a pipette tip array can fill all the holes in a loading block. When a device of the present invention is filled with an array of pipette tip units and actuated, a one-layer pipette tip array would be ejected into an empty loading block 26, thus filling it, in some embodiments. Each pipette tip unit comprises 2, 3, 4, 5, 6, 7, 8, 9, 10, 11, 12, 13, 14 or more nested pipette tips in some embodiments. The pipette tips often are nested continuously, and there often are no intermediate plates or intermediate components between the nested pipette tips.

FIGS. 13 and 14 illustrate an embodiment of a pipette tip dispensing device distal barrier plate 70 having a plurality of channels 76, where each channel has a diameter larger than the widest portion of a pipette tip, which can be the major outer transverse dimension 46 of a pipette tip or the largest outer diameter of the proximal portion of a pipette tip. The barrier plate 70 in FIGS. 13 and 14 has a substantially flat top surface 82, and a substantially flat bottom surface 73 that has a plurality of tails 74 around some or all of channels 76. The bossed arrangement of substantially flat surface 73 having a thickness 79 in conjunction with substantially flat surface 72 is optional, and surface 73 may be continuous to the perimeter of the plate in some embodiments with no bossed region. FIG. 13B illustrates tails 74 extending in a nearly perpendicular orientation from the flat bottom surface 72. The tails 74 around each channel 76 contact the pipette tip, and optionally deflect outwards against the proximal portion of a pipette tip, when a pipette tip is dispensed and passes by the tails 74, thereby imparting a frictional force on the pipette tip when it is dispensed. Distal barrier plate 70 also includes tails 74 with inner surface 75 and optional pins 71.

Figure 13A:
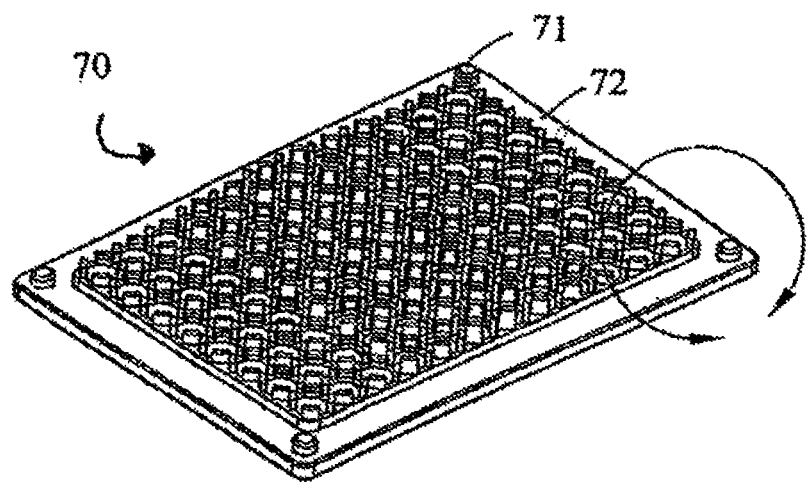
FIG. 13A shows a perspective view of a distal barrier plate with tails pointing in an upward orientation.
Figure 13B:
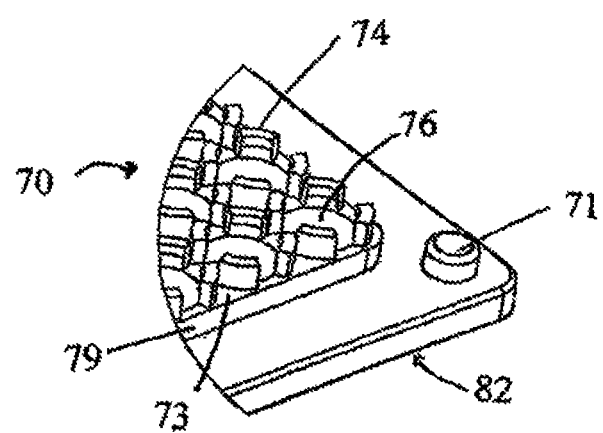
FIG. 13B shows an enlarged cut away view of FIG. 13A (see arrows in FIG. 13A) detailing the tails.
Figure 13C:
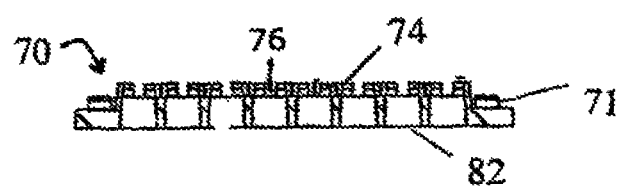
FIG. 13C shows a lateral partial profile view of the tails, where all the tails are the same length.
Figure 13D:
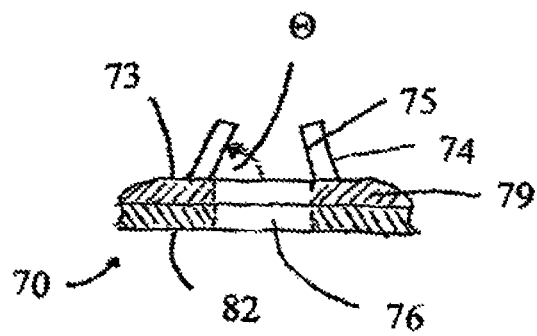
FIG. 13D shows an enlarged cut away, lateral partial profile view of one channel, where the orientation of the each tail is in part defined by an internal angle theta.
Figure 14A:
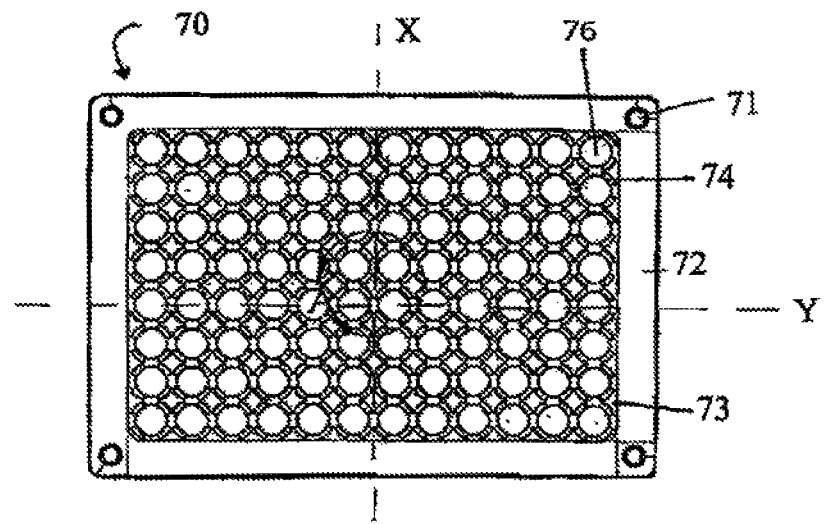
FIG. 14A shows a bottom view of a distal barrier plate with tails arranged in a nearly perpendicular orientation with respect to the bottom surface of the plate.
Figure 14B:
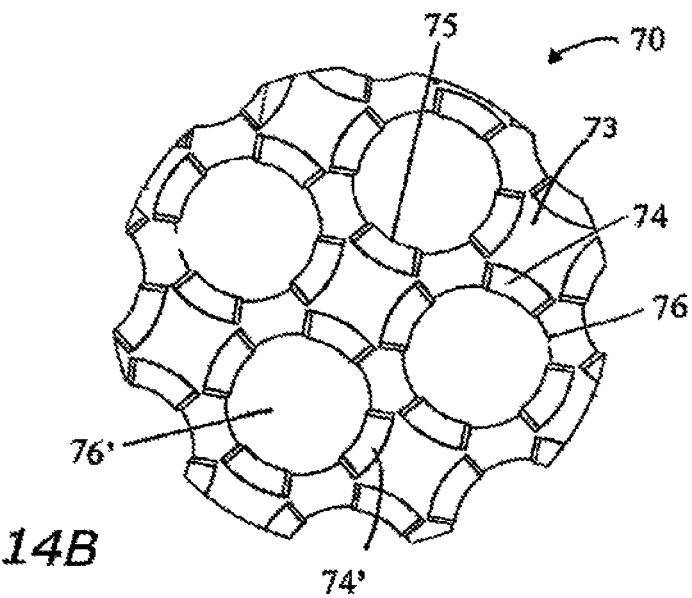
FIG. 14B shows an enlarged cut away view of FIG. 14A (see arrows in FIG. 14A) detailing certain aspects of tails and their orientation to channels.
Figure 14C:
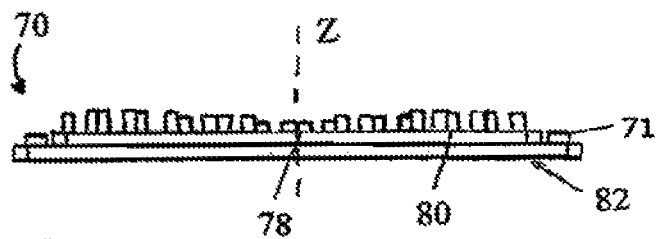
FIG. 14C shows a lateral profile view of the tails, where the tails are varied in length.

Each channel can have 1, 2, 3, 4, 5, 6, 7, 8, 9, 10, 11, 12. 13, 14, 15, 16, 17, 18, 19, 20, 21, 22, 23, 24, 25, 26, 27, 28. 29 or 30 or more tails. FIGS. 13 and 14 illustrate an embodiment of the barrier plate having four tails 74 per channel. FIG. 13 Illustrates an embodiment of the barrier plate where each channel of the barrier plate comprises tails of the same length. FIG. 13B shows an enlarged view of each channel with tails of the same length. FIG. 13C shows a profile view of the tails 74 where they are all of the same length in the barrier plate. FIG. 14C shows an example of channels of the barrier plate having tails of different lengths, where tail 78 is shorter than tail 80. Channels located in the center of the barrier plate can also be the shorter tails, as seen in FIG. 14C. Subsequent channels concentrically disposed about a central longitudinal axis can have progressively longer tails, also seen in FIG. 14C. In some embodiments channels located in the center of the barrier plate can have the longest tails, and in certain embodiments, subsequent channels concentrically disposed about a central longitudinal axis can have progressively shorter tails, which is not shown in FIG. 14C.

Downward movement of the pipette tips within the housing often is achieved by pressure or force, not gravity in most embodiments, and downward movement often is actuated by a user. Downward force or pressure often begins with user-induced activation from the center top of the housing device, with the pressure or axial force greatest at the vertical center. The pressure or axial force then spreads peripherally to the side walls of the housing as well as spreading horizontally, peripherally to the edges of both activator and distal barrier plates.

A user may actuate the device several times, unloading or ejecting an array of pipette tips from the bottom of the distal barrier plate each time. Pipette tips may be dispensed until, for example, the device is empty of pipette tips; insufficient axial force is placed on the device; a force is applied by a user that racks the housing, activator plate and/or distal barrier plate such that pipette tips are not ejected; and/or the actuator housing is at ground level.

It has been determined that providing a distal barrier plate that releases pipette tips in an array at different times is advantageous. A distal barrier plate in which all channels have the same frictional profile ejects all tips of an array at the same time, which requires a particular actuating force by the user or operator, referred to hereafter as total force or "$F_T$." A distal barrier plate in which some channels have a different frictional profile compared to other channels, however, ejects tips in an array at different times. Without being limited by theory, a portion of force $F_T$ first ejects one subset of pipette tips in the array through channels having a first frictional profile, and another portion of $F_T$ then ejects a second subset of pipette tips in the array through channels having a second frictional profile. Thus, releasing tips in an array at different times effectively spreads out $F_T$ over time, and effectively reduces the actuating force required to eject tips of an array at any one point of time.

The term "same frictional profile" as used herein refers to channels in a distal barrier plate that apply the same frictional force to pipette tips in an array for the same amount of time. The term "different frictional profile" refers to a channel in a distal barrier plate that applies a different frictional force and/or applies the same or different frictional force to a pipette tip for a different amount of time, as compared to another channel in the plate.

In some embodiments, a distal barrier plate includes a subset of channels that ejects pipette tips at a rate different than another subset of channels. In certain embodiments, a distal barrier plate includes 2 to 100 different subsets of channels, each of which eject a pipette tip of one array at a different time (e.g., 3, 4, 5, 6, 7, 8, 9, 10, 11, 12, 13, 14, 15, 16, 17, 18, 19, 20, 25, 30, 35, 40, 45, 50, 55, 60, 65, 70, 75, 80, 85, 90, 95 different subsets). Thus, a distal barrier plate can include 2 to 100 different subsets of channels, each of which have a different frictional profile. The time lapse between the time one set of tips is released from one subset of channels to the time another set of tips is released from another subset of channels can be between about 0.00001 seconds to about 5 seconds (e.g., 0.0001, 0.001, 0.01, 0.1, 1 second), and the total time required to eject pipette tips in an array can vary from about 0.001 seconds to about 5 seconds (e.g., 0.01, 0.1, 1 second). In some embodiments, a distal barrier plate is provided in which all channels have the same frictional profile and all dispense pipette tips at the same time.

In some embodiments, pipette tips at or near the center of a distal barrier plate eject first, and pipette tips near the edge of a distal barrier plate eject last. In certain embodiments, subsets of channels disposed in a linear and/or radial orientation away from the center to the periphery of the plate sequentially eject tips at progressively increasing times.

In certain embodiments, pipette tips at or near the center of a distal barrier plate are ejected last, and pipette tips at or near the edge of a distal barrier plate are ejected first. In such embodiments, subsets of channels disposed in a linear and/or radial orientation from the periphery of the plate to the center of the plate sequentially eject tips at progressively increasing times.

Where it is noted herein that a channel applies a particular frictional force to a pipette tip for particular period of time, the channel periphery or channel walls may apply a frictional force to the pipette tip. Often, however, a feature outside a channel applies a frictional force to the pipette tip (e.g., projections or tails around a channel in connection with a top and/or bottom surface of the plate).

Certain features of a distal barrier plate can apply a particular frictional force to a pipette tip. For example, channel features, including but not limited to channel diameter; channel texture; the presence or absence of one or more projections in the channel (e.g., connected to a channel interior wall); the shape, size, length, thickness, width, rigidity, texture, and/or angle of one or more projections in a channel; or combination of the foregoing, can affect the frictional force applied to a pipette tip as it is ejected. Also, the presence or absence of one of more projections outside a channel (e.g., connected to top and/or bottom surface of a distal barrier plate); the shape, size, length, thickness, width, texture and/or angle of one of more projections outside a channel, or a combination of the foregoing, can affect the frictional force applied to a pipette tip as it is ejected.

Any suitable number of projections can be present around or near a channel, including without limitation about 1 to about 50 projections. Projections can contact one or more surfaces of a pipette tip, in some embodiments. Projections can contact the widest portion (e.g., largest diameter portion) of a pipette tip (e.g., proximal region portion), and sometimes do or do not contact lower diameter portions of a pipette tip (e.g., distal region portion). Projections sometimes flex against a portion of a pipette tip (e.g., proximal region portion) when the pipette tip is dispensed past the projections. Projections in some embodiments are elastic, and can return to about the same position after a pipette tip is ejected. Projections in connection with the top surface or bottom surface of a distal barrier plate sometimes are referred to herein as "tails," as described herein.

Projection or tail length can affect the time at which pipette tips are ejected. Without being limited by theory, tails having a relatively longer length apply a frictional force for a longer period of time and result in a tip ejection time that is longer than for relatively shorter tails. FIGS. 14A and 14C show channels located in the center of the barrier plate along the X axis can have tails of the same length and channels along the Y axis can have tails of varying length. In some embodiments, channels located in the center of the barrier plate along the Y axis can have tails of the same length and channels along the X axis can have tails of varying length or channels located in the center of the barrier plate along the X and Y axes comprise tails of varying length, which is not shown. Channels can have an even or odd number of tails. For channels having even number of tails, the tails directly opposite one another around a channel can have the same length. And in certain embodiments tails directly opposite one another around a channel can have a different length. Tails adjacent to one another can also have a different length. The tails can be between 0.01 μm-2.0 mm in length. The tails can be between 0.05 μm-2.0 mm in length. The tails can be about 0.01, 0.02, 0.03, 0.04, 0.05, 0.06, 0.07, 0.08, 0.09, 0.1, 0.12, 0.14, 0.16, 0.18, 0.2, 0.22, 0.24, 0.26, 0.28, 0.30, 0.32, 0.34, 0.36, 0.38, 0.4, 0.42, 0.44, 0.46, 0.48, 0.5, 0.52, 0.54, 0.56, 0.58, 0.6, 0.62, 0.64, 0.66, 0.68, 0.7, 0.72, 0.74, 0.76, 0.78, 0.8, 0.82, 0.84, 0.86, 0.88, 0.9, 0.92, 0.94, 0.96, 0.98, 1.0, 1.2, 1.4, 1.6, 1.8, or 2.0 mm in length, in certain embodiments. A distal barrier plate in some embodiments may include tails having different lengths at different channels (e.g., tails around a first channel have a first length, and tails around a second channel have a second length). For example, in certain embodiments the length of tails for each channel progressively increases or decreases (i) from the center of the X-axis to each end of the X-axis and/or (ii) from the center of the Y-axis to each end of the Y-axis. As used herein, the term "progressive" refers to linear, stepwise, sigmoidal, and exponential, in particular embodiments.

The internal angle of projections or tails also can affect the time at which pipette tips are ejected. For example, a relatively smaller internal angle for tails or projections can result in a relatively longer time required to eject a pipette tip. The term "internal angle" as used herein with respect to a tail around a channel is an angle measured from the midpoint of a channel at the bottom surface of the plate towards the tail surface facing the channel (e.g., surface 75 in FIG. 13D), as illustrated in FIG. 13D as angle theta. For example, an internal angle of 90° from the bottom surface 72 of the distal barrier plate would be exactly parallel to the Z axis as shown in FIG. 13C. Tails of the barrier plate often are nearly perpendicular with respect to, and often are at an internal angle of almost 90° from, the bottom surface 72 of the distal barrier plate. In some embodiments, tails 74 are at an internal angle of about 89° to about 80° from the bottom surface 72 of the distal barrier plate. Tails can be at an internal angle between 88-85°, 87-84°, 86-83° or 86-85° from the bottom surface of the distal barrier plate. Tails are at an internal angle of about 87° from the bottom surface of the distal barrier plate in some embodiments. A distal barrier plate in some embodiments may include tails having different angles at different channels (e.g., tails around a first channel have a first internal angle, and tails around a second channel have a second internal angle). For example, in certain embodiments the internal angle of tails for each channel progressively increases or decreases (i) from the center of the X-axis to each end of the X-axis and/or (ii) from the center of the Y-axis to each end of the Y-axis.

Texture of tails or projections can affect the time required to eject a pipette tip from a distal barrier plate. In some embodiments, texture can modulates the length, thickness or angle of a tail. Tails can comprise smooth surfaces in some embodiments, and in certain embodiments, tails can comprise texture on one or more surfaces. A tail can be entirely smooth, may be entirely textured, or may include textured and smooth surfaces, in some embodiments. A plate can comprise tails that are smooth and some tails that comprise texture. Tail texture can include, without limitation, ridges, barbs, grooves, grains, embossed, etches, pores, pits, lines, scratches, scores, scrapes, cuts, carvings, incisions and the like. Tail texture can increase frictional force on pipette tips moving past the tails when dispensed. Texture also can aid in channeling pipette tips through the tails and into the loading block 26 (e.g., linear or twisted grooves (e.g., rifled grooves) extending from a tail top to tail bottom). A distal barrier plate in some embodiments may include tails having different textures at different channels (e.g., tails around a first channel have a first texture that applies a first frictional force to pipette tips, and tails around a second channel have a second texture that applies a second frictional force to pipette tips). For example, in certain embodiments the texture of tails for each channel progressively increases or decreases the frictional force (i) from the center of the X-axis to each end of the X-axis and/or (ii) from the center of the Y-axis to each end of the Y-axis.

Tails around a channel often are not in the channel, and the portion of a tail joined to the distal barrier plate bottom surface sometimes is co-extensive with the edge of a channel. In some embodiments, the base portion of a tail joined to the distal barrier plate bottom surface is displaced a distance from the channel perimeter that it surrounds, which distance can be a mean, nominal, average or maximum distance of about 0.001 millimeters to about 2 millimeters (e.g., the portion of the tail closest to the channel perimeter that the tail surrounds is offset 0.005, 0.01, 0.05, 0.1, 0.5 or 1 millimeters from the perimeter). The term "displaced" as used herein with respect to tail orientation refers to displaced away from channel perimeter such that the tail base is partially over the channel perimeter, or displaced away from the channel perimeter so that there is a gap between the channel perimeter and the tail base on the plate bottom surface equal to the displaced distance. Thus, the term "surrounds" as used herein with respect to a tail refers to a tail associated with a channel, where the tail base is co-extensive with, or displaced towards or away from, the channel perimeter. For example, tail 74 surrounds channel 76, and tail 74' surrounds channel 76', but tail 74 does not surround channel 76', as shown in FIG. 14B.

Tails described herein generally are not prone to breakage as pipette tips are dispensed through a distal barrier plate comprising the tails. Without being limited by theory, the nearly perpendicular orientation of tails with respect to the bottom surface of a distal barrier plate contributes to tail stability, as this orientation requires little flexion of tails to apply a force to the pipette tips. In certain embodiments, the maximum, mean, median or nominal tail flexion is about 0.01 degrees to about 10 degrees (e.g., about 0.05, 0.1, 0.5, 1, 2, 3, 4, 5, 6, 7, 8, 9 degrees). The term "flex outward" as used herein refers to a tail flexing a certain number of degrees added to the internal angle. For example, a tail that flexes outwards by 2 degree adds 2 degrees to the internal angle in the flexed state; if the tail in the unflexed state has an internal angle of 87 degrees, the tail in the flexed state has an internal angle of 89 degrees. In certain embodiments, no more than 1, 2, 3, 4, 5, 6, 7, 8, 9 or 10 tails, or portions thereof, are separated from the distal barrier plate for a set of 480 pipette tips dispensed through the plate.

A tail may have any convenient shape. A surface of a tail, can be of a shape that includes without limitation, square, rectangle, rhombus, parallelogram, circle, oval, arced, curved, planar, non-planar, and the like. The thickness of a tail can be continuous or tapered (e.g., tapered towards the top (i.e., in association with the plate) or bottom (i.e., at the tail terminus) of the tail).

In some embodiments, the housing can have an actuator housing with a top portion, four sides, an inner surface, and a plurality of regularly spaced detent members disposed on at least one side of the housing, and an alignment housing with an outside surface in contact with the inside surface of the actuator housing in a sliding arrangement, a plurality of regularly spaced detent members configured to releasably engage the detent members of the actuator housing and having a regular spacing that is substantially the same as the regular spacing of the detent members of the actuator housing, and a proximal opening having an inside surface configured to engage outer lateral sides of a loading block 26.

The housing can be made from a polymer material. The polymer material of the housing can be molded polypropylene, or any suitable polymer, including, but not limited to polyethylene (PE), high-density polyethylene, low-density polyethylene, polyethylene teraphthalate (PET, e.g., bio-PET), polyvinyl chloride (PVC), polyethylenefluoroethylene (PEFE), polystyrene (PS), high-density polystryrene, acrylnitrile butadiene styrene copolymers, crosslinked polysiloxanes, polyurethanes, (meth)acrylate-based polymers, cellulose and cellulose derivatives, polycarbonates, ABS, tetrafluoroethylene polymers, corresponding copolymers and the like, and combinations of the foregoing. The polymer material of the housing can have a thickness of about 0.005 inches to about 0.05 inches. The actuator housing can have a telescoping arrangement having multiple housing elements.

The alignment housing can have an optional flange that serves as a footing, in some embodiments. The flange can add extra stability to the housing and can help to ground the housing unit so that no unwanted horizontal movement can occur.

The actuator plate 18 can have a member on the top portion of the actuator that maintains contact with and restricts lateral displacement of the proximal portion of the pipette tips. The member can be selected from the group consisting of foam, a raised grid, a plurality of proximal alignment members 16 and the like. FIG. 1 shows the proximal alignment members 16 on the top portion of the activator plate 18. The proximal alignment members can aid in aligning stacked columns of pipette tips to each channel in the distal barrier plate, which is associated with each empty hole in a loading block 26 where an ejected pipette tip is placed. The member selected can be any material or combination of materials known to one of skill in the art. The member is placed to prevent unwanted vertical or horizontal movement of the pipette tips during storage or activation of the device.

Static charge can develop on pipette tips during use or shipping. This static charge can remain on the tips as they reside in dispensers or trays because there often is no flow or discharge of the electric charge from the tips to a ground source. Static charge in/on the tips and other components of a tray or dispenser may cause some of the tips to repel away from each other and other tray or dispenser components. This repulsion can result in the tips arranged in a different orientation than intended, and can negatively impact interaction with pipette devices (e.g., automated dispensers).

In certain embodiments, the pipette tips are in contact with an electrically conductive member, or a portion thereof, which is in communication with the exterior of the housing. This contact can allow static charge from the pipette tips to be discharged. The contact of an electrically conductive member, or a portion thereof, sometimes is with top proximal edges of tips, which may involve direct, indirect, and/or effective communication with the inner portion of the housing, activator plate, distal barrier plate, loading block, combination thereof, or component thereof. The contact sometimes is with the sides of tips which may be in direct, indirect, and/or effective communication with the housing, activator plate, distal barrier plate, loading block, combination thereof, or component thereof. In some embodiments, an electrically conductive member, or a portion thereof, is in direct, indirect, and/or in effective communication with the pipette tips which ultimately aids in discharging the static charge in/on the pipette tips. The electrically conductive member, or a portion thereof, may be in effective communication with any component or components of the device and be in effective communication with the exterior housing. In certain embodiments, an electrically conductive member, or a portion thereof, is located in any of components of the device such as for example, the actuator housing, alignment housing, activator plate, distal barrier plate, channel, tail and the like, or a component thereof, or a combination of the foregoing, that is in effective communication with the pipette tips, and is exposed through the housing sides or flanges.

An electrically conductive member may comprise any type of electrically conductive material known, such as a conductive metal, for example. Examples of conductive metals include, without limitation, platinum (Pt), palladium (Pd), copper (Cu), nickel (Ni), silver (Ag) and gold (Au). The metals may be in any form in or on the conductive member, for example, such as metal flakes, metal powder, metal strands or coating of metal. An electrically conductive member, or portions thereof, may comprise a metal, polymeric material, foam, film, sheet, foil, salt or combinations thereof. In some embodiments, a conductive metal foil may be utilized for one or more components of a pipette tip device (e.g., copper-aluminum foil; label adhered to an electrically conductive tab on exterior of the housing component). The electrically conductive materials, or portions thereof, may be any material that can contain movable electric charges, for example such as carbon. In some embodiments, the electrically conductive member comprises about 5% to about 40% or more carbon by weight (e.g., 7-10%, 9-12%, 11-14%, 13-16%, 15-18%, 17-20%, 19-22%, 21-24%, 23-26%, 25-28%, 27-30%, 29-32%, 32-34%, 33-36%, or 35-38% carbon by weight). In certain embodiments, an electrically conductive film is utilized that includes carbon (e.g., commercially available from Gemini Plastic Enterprises, Inc., California). An electrically conductive film in some embodiments contains ethylene vinyl acetate (EVA), which can impart a supple quality to the film (e.g., about 5% to about 25% EVA by weight; about 6, 7, 8, 9, 10, 11, 12, 13, 14, 15, 16, 17, 18, 19, 20, 21, 22, 23, 24% EVA). In some embodiments a conductive tab may be in effective communication with any one or combination or all of the components of the device and aid in discharging an electrical charge from the device. A tab often is in effective communication with a conductive material contacting the pipette tips and the exterior of the device (e.g., exterior surface of the housing). The tab may be affixed to one or more portions of a device (e.g., by an electrically conductive label).

The term "effective communication" as used herein refers to direct (e.g., part of the conductive member) or indirect (e.g., via component not part of the conductive member) in communication with exterior of the housing. The term "exposure of conductive member" as used herein may refer to exposure by a reveal in a plate or member which may extend to the housing exterior or can be free hanging or may be affixed to an external surface of the housing and/or loading block. The external surfaces of the housing are for example the sides or bottom of the actuator or alignment housing. The external surfaces of the housing are for example the roof or sides of the housing. The term "affixed" as used herein refer to attachment for example such as embossed or adhesive.

The entirety of each patent, patent application, publication and document referenced herein hereby is incorporated by reference. Citation of the above patents, patent applications, publications and documents is not an admission that any of the foregoing is pertinent prior art, nor does it constitute any admission as to the contents or date of these publications or documents.

Modifications may be made to the foregoing without departing from the basic aspects of the invention. Although the invention has been described in substantial detail with reference to one or more specific embodiments, those of ordinary skill in the art will recognize that changes may be made to the embodiments specifically disclosed in this application, yet these modifications and improvements are within the scope and spirit of the invention.

The invention illustratively described herein suitably may be practiced in the absence of any element(s) not specifically disclosed herein. Thus, for example, in each instance herein any of the terms "comprising," "consisting essentially of," and "consisting of" may be replaced with either of the other two terms. The terms and expressions which have been employed are used as terms of description and not of limitation, and use of such terms and expressions do not exclude any equivalents of the features shown and described or portions thereof, and various modifications are possible within the scope of the invention claimed. The term "a" or "an" can refer to one of or a plurality of the elements it modifies (e.g., "a reagent" can mean one or more reagents) unless it is contextually clear either one of the elements or more than one of the elements is described. The term "about" as used herein refers to a value within 10% of the underlying parameter (i.e., plus or minus 10%), and use of the term "about" at the beginning of a string of values modifies each of the values (i.e., "about 1, 2 and 3" is "about 1, about 2 and about 3"). For example, a weight of "about 100 grams" can include weights between 90 grams and 110 grams. Further, when a listing of values is described herein (e.g., about 50%, 60%, 70%, 80%, 85% or 86%) the listing includes all intermediate and fractional values thereof (e.g., 54%, 85.4%). Thus, it should be understood that although the present invention has been specifically disclosed by representative embodiments and optional features, modification and variation of the concepts herein disclosed may be resorted to by those skilled in the art, and such modifications and variations are considered within the scope of this invention.

Embodiments of the invention are set forth in the claim(s) that follow(s).

What is claimed is:

1. A method for simultaneously dispensing an array of pipette tips into a loading block, comprising:
    (a) providing a dispensing device that includes an array of nested pipette tip units and a distal barrier plate comprising a substantially flat top surface, a substantially flat bottom surface, a first subset of channels and a second subset of channels, wherein each channel has a diameter larger than the widest portion of a pipette tip each of which nested pipette tip units is aligned with a channel in the distal barrier plate, whereby a one-layer pipette tip array is aligned with the channels;
    (b) engaging the dispensing device with a loading block such that distal ends of pipette tips are disposed above or within receptacles of the loading block:
    (c) actuating an actuator of the dispensing device so as to simultaneously apply a same axial force on all of the pipette tips in the array of pipette tips, wherein the axial force dispenses the array of pipette tips through the first subset of channels at a different time than the second subset of channels, thereby ejecting the array of pipette tips into respective receptacles in the loading block.

2. The method of claim 1, wherein the channels comprise one or more channel features in or around each of the channels in the first subset of channels and one or more channel features in or around each of the channels in the second subset of channels,
    the one or more channel features in or around each of the channels in the first subset of channels confer a first frictional force to the pipette tips in the array ejected through the first subset of channels and the one or more channel features in or around each of the channels in the second subset of channels confer a second frictional force to the pipette tips in the array ejected through the second subset of channels, and
    the second frictional force is different than the first frictional force.

3. The method of claim 2, wherein the barrier plate comprises 3, 4, 5, 6, 7, 8, 9, 10, 11, 12, 13, 14, 15, 16, 17, 18, 19 or 20 of different subsets of channels, and each subset ejects pipette tips of one array at different times.

4. The method of claim 3, wherein each subset of channels apply a different frictional force to pipette tips in the array than the other subsets of channels.

5. The method of claim 2, wherein the one or more channel features that confers a different frictional force comprise channel diameter.

6. The method of claim 2, wherein the one or more channel features that confers a different frictional force comprises channel texture.

7. The method of claim 2, wherein the one or more channel features that confers a different frictional force is selected from the group consisting of: one of more projections around the channels and extending from the top surface of the barrier plate; one of more projections around the channels and extending from the bottom surface of the barrier plate; and one of more projections around the channels and extending from the top surface and the bottom surface of the barrier plate.

8. The method of claim 2, wherein the one or more channel features that confers a different frictional force comprise projections and the projections around the first subset of channels have one or more projection features different than the projections around the second subset of channels, which projection features are chosen from shape, size, length, thickness, width, texture, angle or a combination thereof.

9. The method of claim 8, wherein the channels comprise four (4) or more projections around each channel in the first subset of channels and four (4) or more projections around each channel in the second subset of channels.

10. The method of claim 8, wherein the projections around each channel in the first subset of channels extend at an internal angle of about 90 degrees from the bottom surface of the distal barrier plate.

11. The method of claim 8, wherein the projections around each channel in the first subset of channels extend at an internal angle of about 89° to about 80° from the bottom surface of the distal barrier plate.

12. The method of claim 8, wherein (a) the projections around each channel in the first subset of channels are not in the channels or (b) the projections around each channel in the second subset of channels are not in the channels.

13. The method of claim 8, wherein the projection feature comprises length.

14. The method of claim 13, wherein the projections around each channel in the first subset of channels independently are about 0.01 micrometers to about 2.0 millimeters in length.

15. The method of claim 13, wherein the barrier plate comprises a first, a second and a third subset of channels wherein,
   the second subset of channels surround the first subset of channels and the projection features of the first subset of channels are longer than the projection features of the second subset of channels; and,
   the third subset of channels surround the second subset of channels and the projection features of the second subset of channels are longer than the projection features of the third subset of channels.

16. The method of claim 13, wherein the barrier plate comprises a first, a second and a third subset of channels wherein,
   the second subset of channels surround the first subset of channels and the projection features of the first subset of channels are shorter than the projection features of the second subset of channels; and,
   the third subset of channels surround the second subset of channels and the projection features of the second subset of channels are shorter than the projection features of the third subset of channels.

17. The method of claim 1, wherein the time lapse between the time the pipette tips are released from the first subset of channels to the time the pipette tips are released from the second subset of channels is about 0.00001 seconds to about 5 seconds.

18. The method of claim 17, wherein the time lapse between the time the pipette tips are released from the first subset of channels to the time the pipette tips are released from the second subset of channels is about 0.0001 seconds to about 1 second.

19. The method of claim 17, wherein the total time required to eject all of the pipette tips in the array is about 0.001 seconds to about 5 seconds.

20. The method of claim 19, wherein the total time required to eject all of the pipette tips in the array is about 0.01 seconds to about 1 second.

21. The method of claim 1, wherein barrier plate comprises 96, 384 or more channels.

22. The method of claim 1, wherein the barrier plate comprises a polymer.

23. The method of claim 1, wherein the actuator comprises an actuator housing and an alignment housing; wherein each of the actuator housing and alignment housing comprises a clear polymer material to visualize ejection of the pipette tips during actuation.

24. The method of claim 23, wherein the actuator housing comprises a telescoping arrangement having multiple housing elements and wherein actuation of the actuator comprises collapsing the multiple housing elements from an extended state to a collapsed nested state.

* * * * *